US012218609B2

(12) United States Patent
Lee et al.

(10) Patent No.: US 12,218,609 B2
(45) Date of Patent: Feb. 4, 2025

(54) VIRUS-BASED PIEZOELECTRIC ENERGY GENERATION

(71) Applicant: The Regents of the University of California, Oakland, CA (US)

(72) Inventors: Seung-Wuk Lee, Walnut Creek, CA (US); Byung Yang Lee, Seoul (KR)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 3004 days.

(21) Appl. No.: 13/892,148

(22) Filed: May 10, 2013

(65) Prior Publication Data

US 2021/0320597 A1     Oct. 14, 2021

Related U.S. Application Data

(60) Provisional application No. 61/646,213, filed on May 11, 2012.

(51) Int. Cl.
| | |
|---|---|
| H02N 2/00 | (2006.01) |
| C12N 7/00 | (2006.01) |
| H02N 2/18 | (2006.01) |
| H10N 30/06 | (2023.01) |
| H10N 30/30 | (2023.01) |
| H10N 30/87 | (2023.01) |

(52) U.S. Cl.
CPC ............... *H02N 2/00* (2013.01); *C12N 7/00* (2013.01); *H02N 2/18* (2013.01); *H10N 30/06* (2023.02); *H10N 30/30* (2023.02); *H10N 30/874* (2023.02); *H10N 30/878* (2023.02); *C12N 2795/00021* (2013.01)

(58) Field of Classification Search
CPC ... H02N 2/00; H02N 2/18; C12N 7/00; C12N 2795/00021; C12N 2795/14121; C12N 2795/14122; C12N 2795/14131; H10N 30/06; H10N 30/30; H10N 30/874; H10N 30/878; H10N 30/704; H10N 30/857; C07K 14/005
See application file for complete search history.

(56) References Cited

U.S. PATENT DOCUMENTS

| | | | | |
|---|---|---|---|---|
| 2002/0088284 | A1* | 7/2002 | Takeuchi | H10N 30/302 73/865 |
| 2005/0016276 | A1* | 1/2005 | Guan | G01N 29/036 73/579 |
| 2006/0292554 | A1* | 12/2006 | Held | C40B 40/02 435/235.1 |
| 2009/0092965 | A1* | 4/2009 | Weiss | G01N 27/327 435/5 |
| 2010/0092508 | A1* | 4/2010 | Bachmann | A61P 25/36 530/391.1 |

OTHER PUBLICATIONS

Wang et al, Anal. Bioanal. Chem., vol. 415, pp. 3927-3944, published Mar. 3, 2023.*
Weiss et al, Prot. Sci., vol. 9, pp. 647-654, published Apr. 2000.*
P. Rakbamrung et al., Performance comparison of PZT and PMN-PT piezoceramics for vibration energy harvesting using standard or nonlinear approach. Sens. Actuators, A Phys. 163, 493 (2010).
D. A. Marvin, et al., Molecular Structure of fd (f1, M13) Filamentous Bacteriophage Refined with Respect to X-ray Fibre Diffraction and Solid-state NMR Data Supports Specific Models of Phage Assembly at the Bacterial Membrane. J. Mol. Biol. 355, 294 (2006).
S. R. Anton and H.A Sodano. A review of power harvesting using piezoelectric materials (2003-2006). Smart Mater. Struct. 16, R1-R21 (2007).
Z. L. Wang and J. Song. Piezoelectric nanogenerators based on zinc oxide nanowire arrays. Science. 312, 242 (2006).
S. Xu et al., Self-powered nanowire devices. Nat. Nanotechnol. 5, 366 (2010).
Y. Qin, X. D. Wang, Z. L. Wang, Microfibre-nanowire hybrid structure for energy scavenging. Nature 451, 809 (2008).
X. Chen, S. Y. Xu, N. Yao, Y. Shi, 1.6 V nanogenerator for mechanical energy harvesting using PZT nanofibers. Nano Lett. 10, 2133 (2010).
Y. Hu, Y. Zhang, C. Xu, G. Zhu, Z. L. Wang, High-output nanogenerator by rational unipolar assembly of conical nanowires and its application for driving a small liquid crystal display. Nano Lett. 10, 5025 (2010).
G. Zhu, R. Yang, S. Wang, Z. L. Wang, Flexible high-output nanogenerator based on lateral ZnO nanowire array. Nano Lett. 10, 3151 (2010).
C. Chang, V. H. Tran, J. Wang, Y.-K. Fuh, L. Lin, Flexible high-output nanogenerator based on lateral ZnO nanowire array. Nano Lett. 10, 726 (2010).
Y. Saito et al., Lead-free piezoceramics. Nature 432, 84 (2004).
M. Minary-Jolandan and M. F. Yu, Nanoscale characterization of isolated individual type I collagen fibrils: polarization and piezoelectricity. Nanotechnology 20, 6 (2009).
A. A. Marino, J. A. Spadaro, E. Fukada, L. D. Kahn, R. O. Becker, Piezoelectricity in collagen films. Calcif. Tissue Int. 31, 257 (1980).
E. Korostoff, Stress generated potentials in bone: relationship to piezoelectricity of collagen. J. Biomech. 10, 41 (1977).

(Continued)

*Primary Examiner* — Narayan K Bhat
(74) *Attorney, Agent, or Firm* — Robin C. Chiang; LAWRENCE BERKELEY NATIONAL LABORATORY

(57) ABSTRACT

The present invention provides for a modified virus, such as a recombinant M13 phage, which in an array, such as a film, is capable of producing piezoelectricity. The modified virus comprises a coat protein can displays a negatively charged amino acid sequence. The present invention provides for a device comprising a piezoelectric element comprising a suitable virus, such as the modified virus, a first surface and a second surface, wherein the first surface is in contact with a first electrode and the second surface is in contact with a second electrode, wherein when pressure is applied to the film, the film is capable of generating an electric current. The present invention provides for a method of making the device, and a method for generating electricity using the device.

31 Claims, 12 Drawing Sheets
Specification includes a Sequence Listing.

(56) References Cited

OTHER PUBLICATIONS

J. L. F. Weytjens, D. A. Viberg, A. A. Caputi, K. Kallesoe, J. A. Hoffer, New transducers for measuring muscle length in unrestrained animals. J. Neurosci. Methods 45, 217 (1992).

S.-W. Lee, C. Mao, C. E. Flynn, A. M. Belcher, Ordering of quantum dots using genetically engineered viruses. Science 296, 892 (2002).

C. B. Mao et al., Virus-based toolkit for the directed synthesis of magnetic and semiconducting nanowires. Science 303, 213 (2004).

M. T. Klem, M. Young, T. Douglas, Biomimetic synthesis of β-TiO2 inside a viral capsid. J. Mater. Chem. 18, 3821 (2008).

D. M. Kuncicky, R. R. Naik, O. D. Velev, Rapid deposition and long-range alignment of nanocoatings and arrays of electrically conductive wires from tobacco mosaic virus. Small 2, 1462 (2006).

Y. J. Lee et al., Fabricating genetically engineered high-power lithium-ion batteries using multiple virus genes. Science 324, 1051 (2009).

K. T. Nam et al., Virus-enabled synthesis and assembly of nanowires for lithium ion battery electrodes. Science 312, 885 (2006).

K. T. Nam et al., Stamped microbattery electrodes based on self-assembled M13 viruses. Proc. Natl. Acad. Sci. U. S. A. 105, 17227 (2008).

A. Merzlyak, S. Indrakanti, S. W. Lee, Genetically engineered nanofiber-like viruses for tissue regenerating materials. Nano Lett. 9, 846 (2009).

S. V. Kalinin, D. A. Bonnell, Imaging mechanism of piezoresponse force microscopy of ferroelectric surfaces. Phys. Rev. B 65, 125408 (2002).

S. Y. Yoo, W.-J. Chung, T. H. Kim, M. Le, S.-W. Lee, Facile patterning of genetically engineered M13 bacteriophage for directional growth of human fibroblast cells. Soft Matter 7, 363 (2011).

C. Durkan, M. E. Welland, D. P. Chu, P. Migliorato, Probing domains at the nanometer scale in piezoelectric thin films. Phys. Rev. B 60, 16198 (1999).

T. Jungk, A. Hoffmann, E. Soergel, Contrast mechanisms for the detection of ferroelectric domains with scanning force microscopy. New J. Phys. 11, (2009).

A. Merzlyak, S.-W. Lee, Engineering phage materials with desired peptide display: rational design sustained through natural selection. Bioconjugate Chem. 20, 2300 (2009).

Z. Wang, J. Hu, A. P. Suryavanshi, K. Yum, M.-F. Yu, Voltage generation from individual BaTiO(3) nanowires under periodic tensile mechanical load. Nano Lett. 7, 2966 (2007).

\* cited by examiner

A. Engineered Phages

B. Ionic Concentration

C. Pulling Speed     D. Pulling Time

VIRUS-BASED PIEZOELECTRIC ENERGY GENERATION

CROSS-REFERENCE TO RELATED APPLICATIONS

This application claims priority to U.S. Provisional Patent Application Ser. No. 61/646,213, filed on May 11, 2012, which is hereby incorporated by reference.

STATEMENT OF GOVERNMENTAL SUPPORT

The invention described and claimed herein was made in part utilizing funds supplied by the U.S. Department of Energy under Contract No. DE-AC02-05CH11231. The government has certain rights in this invention.

FIELD OF THE INVENTION

This invention relates generally to recombinant bacteriophages.

BACKGROUND OF THE INVENTION

Piezoelectric materials are an attractive means of producing renewable and clean energy, utilizing ubiquitous vibrational or mechanical energy sources in everyday life (1). The piezoelectric effect can be defined as the inter-conversion between mechanical and electrical energies induced by charge redistribution and separation upon application of mechanical or electrical stimuli to materials without an inversion center (2). Various inorganic piezoelectric materials, such as lead zirconate titanate (PZT), litium niobate, and barium titanate, exhibit strong piezoelectric properties and have been used to generate electrical energy through daily events, such as floor-based generation of electricity through the collection of foot steps (3). Recently, a variety of nanomaterials have been used to efficiently produce electrical energy by scavenging vibrational energy to operate various electronic devices. Many inorganic nanostructured materials, such as aligned ZnO or PZT nanowires/nanofibers, have been developed to produce electrical signals up to ~1.5 V and ~26 nA, enough to operate various small electronic devices (4-9). Aligned electro-spun organic nanofibers (polyvinylidene fluoride or polyimide) have exhibited piezoelectric energy conversion efficiencies an order of magnitude higher than those of bulk films (10). Although previous piezoelectric materials have provided useful schemes for energy generation, they are made using environmentally harmful chemicals and/or energy expensive processes such as high temperature, high electric field, and extreme-pressurized conditions (11). In nature, however, various biological piezoelectric materials, such as α-helical proteins, DNA, and collagens (12-14), are naturally produced and integrated into tissues and organs: orchestrating bodily functions such as the contraction of muscles, and the remodeling of bone matrices (13, 15, 16). Although biopiezoelectricity is efficient and plays an essential role in natural systems, it is rarely utilized within engineering materials. This is mainly due to a lack of cost effective fabrication methods for biopiezoelectric materials and little understanding of how to control their properties at a molecular level.

SUMMARY OF THE INVENTION

The present invention provides for a modified virus suitable for use in the piezoelectric element of a device of the present invention. The modified virus is a recombinant virus. The suitable virus comprises a capsid (or shell) that has a helical, icosahedral, or complex symmetry. The suitable virus comprises a plurality of aligned coat proteins comprising at least one amino acid sequence presented on the surface of the naked or enveloped virus. The virus, in whole or in part, possesses an electric dipole moment. The plurality of coat proteins comprises (i) one plurality of coat proteins of identical amino acid sequence, or (ii) two or more pluralities of coat proteins, wherein each plurality comprises coat proteins having identical amino acid sequence.

In some embodiments, the suitable virus is a bacteriophage. In some embodiments, the suitable virus is an animal virus. In some embodiments, the suitable virus is a DNA or a RNA virus. In some embodiments, the suitable virus is a virus with a linear or circular genome. In some embodiments, the suitable virus has a double-stranded or single-stranded genome. In some embodiments, the suitable virus comprises a capsid (or shell) that has a helical, icosahedral, or complex symmetry. In some embodiments, the coat protein of the capsid is recombinant. In some embodiments, the suitable virus is a recombinant M13 phage comprising a coat protein, such as pVIII, that displays a negatively charged amino acid sequence, with the proviso that the sequence is not the wild-type sequence of M13. The invention provides for a recombinant nucleic acid encoding a genome of the modified virus. In some embodiments, the recombinant nucleic acid is capable of replicating the modified virus of the present invention. In some embodiments, the recombinant nucleic acid encodes a recombinant M13 bacteriophage genome capable of replicating the recombinant M13 bacteriophage of the present invention. The recombinant nucleic acid can also be a replicon in a suitable microorganism, such as bacterial host cell, such as $E.$ $coli$. Nucleic acid sequences and methods of maintaining and replicating such replicons are well known to one skilled in the art.

The present invention provides for a device comprising a piezoelectric element comprising an array of a suitable virus. In some embodiments, the array is a film of a suitable virus of the present invention comprising a first surface and a second surface, wherein the first surface is in contact with a first electrode and the second surface is in contact with a second electrode. In some embodiments, the device is a charge generator. In some embodiments, the phage film comprises a two-dimensional (2D) surface area, wherein each surface area has an area of equal to or more than about 1 cm$^2$. In some embodiments, the phage film comprises a thickness of equal to or more than about 10 μm. In some embodiments, the phage film has a capacitance of equal to or more than about 265 pC. When pressure is applied to the phage film, the phage film is capable of generating piezoelectricity or electricity. The suitable virus can be a wild-type virus, a wild-type virus lacking its envelop or membrane, or a modified virus of the present invention.

The invention provides for making a phage film of the present invention, comprising: providing a plurality of suitable virus, and allowing for self-alignment or applying an external force to align the plurality of the suitable virus.

The present invention provides for a method of making a device of the present invention. In some embodiments the method comprises: (a) providing a plurality of suitable virus, (b) assembling of the plurality of suitable virus into a monolayer of the plurality on a suitable substrate, and (c) optionally assembling the monolayer into a plurality of two or more monolayers.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
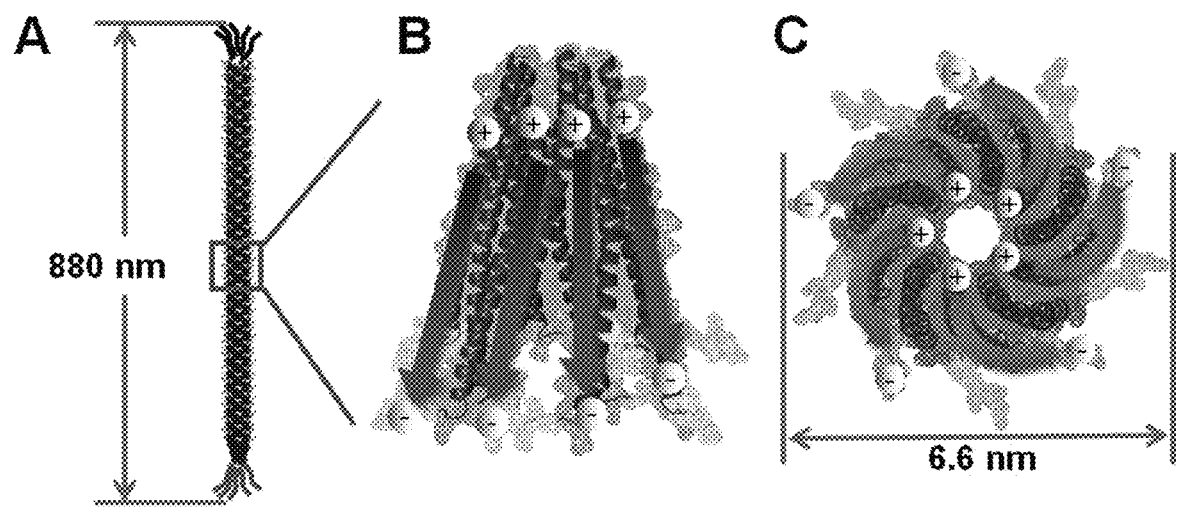
FIG. 1. Schematic diagram of piezoelectric M13 phage structure. (A) The phage is about 880 nm in length and about 6.6 nm in diameter. The phage is covered by 2700 copies of pVIII proteins and has 5 copies of pIII (red-line) and pIX proteins (black-line) at both ends. (B) Side view of the aligned charged dipole structure from ten major coat proteins in the phage showing the α-helical structures with dipole moments pointing from the N-terminus to C-terminus. (C) Vertical cross-sectional view of the phage showing the 5-fold rotational and 2-fold screw symmetry. The colored arrows represent the coat protein dipoles from positive (blue) to negative (red).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptide" includes a plurality of such peptides, and so forth.

These and other objects, advantages, and features of the invention will become apparent to those persons skilled in the art upon reading the details of the invention as more fully described below.

Modified Virus

The present invention provides for a modified virus suitable for use in the device of the present invention. The term "modified virus" defines a virus that is modified in such a way that the modified virus is not naturally occurring. The term "suitable virus" defines any virus that is suitable for use in the device of the present invention, wherein the virus can be (1) a naturally occurring or wild-type virus, (2) a virus lacks a membrane or envelop wherein the naturally occurring or wild-type virus has a membrane or envelop, and (3) a modified virus of the present invention, wherein the suitable virus has possesses one or more intrinsic piezoelectric properties.

The suitable virus or modified virus can be a virus of one of the following categories found in Table 1.

TABLE 1

| Nucleic Acid | Capsid Symmetry | Naked or enveloped | Genome Architecture | Baltimore Class |
|---|---|---|---|---|
| RNA | Icosahedral | Naked | ds | III |
| | | | (+) ss | IV |
| | | Enveloped | (+) ss | IV |
| | | | (+) ss 2 copies | VI |
| | Helical | Enveloped | (+) ss | IV |
| | | | (−) ss | V |
| DNA | Icosahedral | Naked | ss linear (+) or (−) | II |
| | | | ss circular | II |
| | | | ds circular | I |
| | | | ds linear | I |
| | | Enveloped | ds circle gapped | I |
| | | | ds linear | I |
| | | Naked/enveloped (cytoplasmic) | ds linear | I |
| | Complex | Enveloped (cytoplasmic) | ds covalently joined ends | I |

"ds": double-stranded; "ss": single-stranded; "(+)": positive strand; (−): negative strand.

In some embodiments, the suitable or modified virus comprises a coat protein that displays a negatively charged amino acid sequence on the surface of the virus. The present invention provides a matrix comprising an array of a plurality of the suitable or modified virus of the present invention. The negatively charged amino acid sequence is a peptide of any suitable length that does not interfere with the self-assembly of the virus. The modified virus can be made in by methods known to one skilled in the art.

One skilled in the art can engineer the modified virus. The suitable or modified virus can be assemble, such as self-assembled, into a directionally ordered liquid crystalline structure, such as a two-dimensional (2D) monolayer film or multi-layer films.

In some embodiments, the modified virus is a recombinant M13 phage suitable for use in the device of the present invention. The recombinant M13 phage comprises a coat protein, such as pVIII, that displays a negatively charged amino acid sequence, with the proviso that the sequence is not the wild-type sequence of M13. In some embodiments, the recombinant M13 phage displays a negatively charged amino acid sequence on all of the M13 major coat protein, such as pVIII, of the capsid of the virus. The present invention provides a matrix comprising an array of a plurality of the recombinant M13 phage of the present invention. The negatively charged amino acid sequence is a peptide of any suitable length that does not interfere with the self-assembly of the M13 phage. The recombinant phages can be made in by the methods taught herein (e.g. Examples 1 and 2), with the appropriate negatively charged amino acid sequence as selected by one skilled in the art.

One skilled in the art can engineer the recombinant M13 bacteriophage. Filamentous M13 phage has several qualities that make them attractive candidates for use in the present invention. The M13 phage has a monodisperse, long-rod shape that enables its self-assembly into directionally ordered liquid crystalline structures, such as two-dimensional (2D) monolayer films or multi-layer films. The M13 phage is a bacterial virus composed of a single-stranded DNA encapsulated by various major and minor coat proteins. It has a long-rod filament shape that is equal to or more than about 880 nm long and equal to or more than about 6.6 nm wide. Through genetic modification, short peptide signaling molecules can be displayed on every copy of the pVIII major coat protein, which covers most of the phage surface (which is equal to or more than 98%). Wild-type M13 has about 2,700 copies of the major coat protein on each M13. A recombinant M13 of the present invention can have equal to or more than 2,700 copies on each recombinant M13.

The M13 phages have several properties that make them ideal for use in the present invention. The M13 phage is non-lytic, producing little cell debris during amplification and simplifying the amplification and purification processes. Therefore, mass amplification of the virus can be easily realized through its infection of *E. coli* cells, resulting in a monodisperse population of the phage. Due to their monodispersity and long-rod shape, phages have the ability to self-assemble and have been extensively studied as highly organized liquid crystalline systems. The concentration of the viral suspension, ionic strength of the solution, and externally applied force fields are used to modulate viral organization in these systems and have previously been optimized for the construction of one-, two-, and three-dimensional phage-based materials. In addition, through the insertion of random gene sequences into the phage genome, a large combinatorial library can be displayed on the phage major and minor coat proteins. It has been demonstrated that semiconductor-specific phage can be isolated from the directed evolutionary screening process of phage display. These phages can synthesize various semiconductor and metallic nanocrystals and can also be self-assembled into periodically ordered films and fibril structures. Such materials and structures can be used to develop high-density data storage and information processing devices.

The invention provides for a recombinant nucleic acid encoding a recombinant M13 bacteriophage genome capable of replicating the recombinant M13 bacteriophage of the present invention. The recombinant nucleic acid can also be a replicon in a suitable microorganism, such as bacterial host cell, such as *E. coli*. Nucleic acid sequences and methods of maintaining and replicating such replicons are well known to one skilled in the art.

In one embodiment, the M13 phage is about 880 nm in length. In one embodiment, the M13 phage is about 6.6 nm in diameter. In some embodiments, each bacteriophage has equal to or more than about 500, 1000, 1500, 2000, or 2500 copies of the coat protein.

Negatively Charged Amino Acid Sequence

In some embodiments, the suitable virus or modified virus comprises a coat protein comprising a negatively charged amino acid sequence which is presented on the surface of the virus. In some embodiments, the suitable virus or modified virus comprises a coat protein comprising a negatively charged amino acid sequence is on or near the N-terminus of the coat protein, such as within the first 50, 40, 30, 20, or 10 amino acid residues at the N-terminus. In some embodiments, the negatively charged amino acid sequence is 3-8 amino acids long. In some embodiments, the negatively charged amino acid sequence comprises one or more negatively charged amino acids, such as one, two, three, four, five or more than five negatively charged amino acids. In some embodiments, the negatively charged amino acid sequence comprises is at most five, six, seven, eight, nine or ten residues long, and does not contain any positively charged amino acids. In some embodiments, the only non-negatively charged amino acid present in the negatively charged amino acid sequence is glycine (G). In some embodiments, the only non-negatively charged amino acid present in the negatively charged amino acid sequence is one or two G. Suitable negatively charged amino acids include naturally occurring and non-naturally occurring amino acids. Suitable examples of naturally occurring negatively charged amino acids are glutamate (E) and aspartate (D). Suitable negatively charged amino acid sequences include, but are not limited to, EG, EE, GE, EEG, EEEG (SEQ ID NO:1), and EEEE (SEQ ID NO:2).

In some embodiments, the M13 bacteriophage comprises a M13 major coat protein comprising a N-terminus comprising a negatively charged amino acid sequence comprising at least two amino acid residues positioned between the first and sixth amino acids of wild-type pVIII. The invention provides for a recombinant nucleic acid encoding a recombinant M13 bacteriophage genome capable of replicating the recombinant M13 bacteriophage of the present invention.

Devices of the Present Invention

The present invention provides for a device comprising a piezoelectric element comprising an array of the suitable virus, a first surface and a second surface, wherein the first surface is in contact with a first electrode and the second surface is in contact with a second electrode. In some embodiments, the array is a 2-dimensional array, such as a film. In some embodiments, the device is a charge generator. In some embodiments, the film comprises a two-dimensional (2D) surface area, wherein each surface area has an area of equal to or more than about 1 cm$^2$. In some embodiments, the film comprises a thickness of equal to or more than about 10 μm. In some embodiments, the film has a capacitance of equal to or more than about 265 pC. When pressure is applied to the piezoelectric element, the piezoelectric element is capable of generating an electric current.

In some embodiments, the device comprises a wild-type M13 or recombinant M13 phage film comprising a surface and a second surface, wherein the first surface is in contact with a first electrode and the second surface is in contact with a second electrode. In some embodiments, the device is a charge generator. In some embodiments, the phage film comprises a two-dimensional (2D) surface area, wherein each surface area has an area of equal to or more than about 1 cm$^2$. In some embodiments, the phage film comprises a thickness of equal to or more than about 10 μm. In some embodiments, the phage film has a capacitance of equal to or more than about 265 pC. When pressure is applied to the phage film, the phage film is capable of generating piezoelectricity or electricity. The M13 phage possesses piezoelectric properties due to the aligned dipole structure originating from the 2700 α-helical coat proteins along its long axis.

In some embodiments, the film comprises a plurality of a genetically engineered virus capable of guiding cell growth and polarization via signaling peptides and directionally aligned structures. The genetically engineered virus is capable of guiding cell growth, migration and/or alignment, providing essential biological effects including proliferation and/or differentiation. In some embodiments, the film comprises a plurality of a genetically engineered M13 bacteriophage capable of guiding cell growth and polarization via signaling peptides and directionally aligned structures. In some embodiments, the genetically engineered phage is capable of guiding cell growth, migration and/or alignment, providing essential biological effects including proliferation and/or differentiation, which can be performed by expressing specific biological motifs, such as the amino acid sequences taught in WO2009/120895, incorporated by reference herein, on their coat proteins, on which functional DNA, proteins and cells can be conjugated and/or fixed thereon.

In one embodiment, the film is a virus-based (such as phage-based) piezoelectric thin film. The piezoelectric strength of the virus can be tuned through genetic engineering of a major coat protein of the virus by the addition or deletion of negatively charged amino acid residues. In one embodiment, the device comprises a plurality of films stacked together in a multi-layer phage film. In one embodiment, the film has a piezoelectric strength of equal to or more than about 7.8 pm/V. In one embodiment, the device can produce equal to or more than about 1 nA, 2 nA, 3 nA, 4 nA, 5 nA, or 6 nA, and/or 100 mV, 200 mV, 300 mV, or 400 mV of electricity. In one embodiment, the device can produce sufficient electricity to power a liquid crystal display or a microelectronic device.

In some embodiments, the suitable virus is bacteriophage M13 comprising coat protein pVIII, and optionally each M13 bacteriophage has equal to or more than about 2,700 copies of pVIII and about five copies of minor coat proteins (pIII and pIX) located at either end. The M13 major coat protein (pVIII) has an α-helical structure with a charged dipole from the carboxy- to amino-terminal direction, covering the phage body with five-fold rotational symmetry. As the resulting aligned protein coat structure of M13 possesses neither a centro-symmetry nor an inversion center, M13 phages possess piezoelectric properties. The piezoelectric properties of the bacteriophage can be measured using a piezoresponse force microscope (PFM), whereby the mechanical response of the material can be monitored during the application of an electrical signal through a metal-coated AFM tip while scanning the sample.

In some embodiments, the film is a single self-assembled phage monolayer films having a surface area with a width equal to or more than about 1 μm, 10 μm, 100 μm, 1 mm, or 1 cm. In some embodiments, the film lies on a suitable conducing substrate, such as an Au substrate. A method of making the phage monolayer film is provided in Examples 1 and 2 herein. The piezoelectric virus responds to an applied electric field in both the lateral and axial directions.

In some embodiments, the piezoelectric strength of the bacteriophage can be modulated by engineering the pVIII coat protein through recombinant DNA techniques. The coat protein dipole is induced mainly by the charge distribution of the pVIII coat proteins (i.e., the rich positively charged residues in the C-terminal region and rich negatively charged residues in the N-terminal region).

In some embodiments, the piezoelectric properties of the virus can be enhanced by controlling the physical structure (i.e., thickness) of the virus film. In some embodiments, the film is a multilayer phage film of varying thicknesses using the M13 4E-phage. The AFM topography image of such a phage film shows that the film possesses a smectic liquid crystalline structure (ordered in both direction and position) with ~900 nm layer spacing. The phage particles formed a ridge and groove band pattern, composed of the pVIII major coat proteins, and the pIII and pIX minor coat proteins, respectively. The $d_{eff}$ of the ridge areas is higher than that of the groove areas. The piezoelectric response of the film is dependent on the film thickness. In some embodiments, the film has an increased effective piezoelectric coefficient with an increased film thickness (such as up to a saturated level of $d_{eff} \approx 3.9$ pm/V for films greater than ~100 nm thick). The $d_{33}$ value of the film is about 7.8 pm/V.

In some embodiments, the device is a phage-based piezoelectric energy generator comprising a 4E-phage film having a size equal to or greater than about 1 $cm^2$ in contact with two electrodes, such as sandwiched between two metal electrodes.

The device can be measured for electrical signal output when a mechanical load is applied to it. One method of measuring the device for electrical signal output is provided in Examples 1 and 2 described herein.

In some embodiments, the device can provide a charge value of equal to or more than about Q~393 pC, when a peak load of about F=34 N is applied.

In some embodiments, the film has a piezoelectric coefficient of equal to or more than about $d_{33}$=11.6 pC/N (pm/V).

In some embodiments, the piezoelectric element further comprises an enhancing material. The enhancing material comprises ZnO, $BaTiO_2$, piezoelectric polymer (such as poly(vinylidene fluoride) (PVDF)), and the like. The ZnO can be in the form of one or more nanowires. Exemplary materials are taught by Lee et al., "A Hybrid Piezoelectric Structure for Wearable Nanogenerators," Adv. Mater. (2012). In some embodiments, there is a plurality of piezoelectric elements in series or in parallel to increase voltage and current, respectively. In some embodiments, the device comprises a large number of piezoelectric elements integrated using a photolithographic method. In some embodiments, the device further comprises the piezoelectric element contacting one or more buffer structures comprising a polymeric organosilicon compound, such as polydimethylsiloxane (PDMS). In some embodiments, the device is surrounded by the buffer structure(s).

In some embodiments, the device has one or more of the properties, including optical properties, described in Examples 1 and 2.

Methods of Making the Invention

The present invention provides for a method of making a device of the present invention. In some embodiments the method comprises: (a) providing a plurality of modified M13 bacteriophage comprising one or more recombinant phage coat protein comprising a N-terminus comprising a negatively charged amino acid sequence, (b) assembling of the plurality of modified M13 bacteriophage into a monolayer of the plurality on a suitable substrate, optionally (c) assembling of the monolayer into a plurality of two or more monolayers. In some embodiments, the assembling takes place on a conducting or semi-conducting material. In some embodiments, the conducting material is a conducting metal such as Fe, Ag, Au, Pt, or the like. In some embodiments, the conducting or semi-conducting material has a thickness of about 100 nm. In some embodiments, the conducting or semi-conducting material is on the suitable substrate, such as a Si substrate, such that the assembling takes place on the conducting or semi-conducting material. In some embodiments, there is an adhesion layer between the conducting or semi-conducting material and the suitable substrate, such as a Ti adhesion layer. In some embodiments, the adhesion layer has a thickness of about 5 nm.

In some embodiments, the method further comprises preparing the substrate prior to the (b) assembling step. In some embodiments, the preparing step comprises passivating the substrate by contacting the substrate with a suitable passivating agent, such as octadecanethiol (ODT) and/or a suitable aminothiol, such as cysteamine. In some embodiments, the preparing step comprises washing with a first suitable solvent, such as ethanol, and optionally blow drying with an inert gas, such as $N_2$. In some embodiments, the preparing step further comprises backfilling any remaining area on the substrate with cysteamine (or any other suitable aminothiol), such as adding 3 mM aqueous cysteamine solution for 2 min, to produce an ODT/cysteamine pattern substrate, and optionally washing the ODT/cysteamine pattern substrate with water, such as DI water, and a second suitable solvent, such as an organic alcohol, such as ethanol, and optionally (h) blow drying with an inert gas, such as $N_2$.

In some embodiments, the (b) assembling step comprises coating a monolayer of phage onto the substrate using a dip-coating method. The dip-coating method comprises vertically dipping the substrate (having a vertical cysteamine stripe pattern) into a solution of the phage. The phage solution can be of any suitable concentration, such as 1 mg/mL in deionized water. The substrate is pulled out at any speed or any constant speed (such as 1.2 cm/h). The phage patterned substrate can then be air dried for 2 h and kept in a desiccator prior to the next step.

Multilayer films are prepared with either the pulling method or the drop-cast method. By the pulling method, multilayer films of thickness up to ~300 nm can be obtained. For liquid crystalline films with thicknesses higher than 300 nm, the drop-cast method is utilized. In some embodiments, about 100 µL of virus solution (about 2 mg/mL in DI water) is dropped onto an Au substrate and kept in a desiccator for about 3 days. The resulting film can comprise one or more regions of smectic phase with highly ordered and well packed viruses. In some embodiments, the pulling method comprises pulling at a rate ranging from about 10 µm/hour to about 3 mm/minute for from about 1.5 to 600 seconds.

Gold-coated flexible substrates are prepared by depositing 10 nm Cr and 30 nm Au on Thermanox films. Then, 200 µL of 5 mg/mL 4E-phage solution are dropped on the gold-coated flexible substrate. The solution is air dried, during which the phages form highly-ordered smectic regions comprising large area ordered structures. After drying, another gold-coated flexible substrate is overlaid on the film. The effective device area, where the phage films and electrodes overlap, can be equal to or more than about 1 $cm^2$. The device is then embedded between two about 2.5 mm thick polydimethylsiloxane (PDMS) films for structural stability. Then signal wires are attached to the gold electrodes.

One method of constructing such M13 bacteriophage is provided in Example 1 herein. Another method is provided in Example 2 herein. The invention provides for making a phage film of the present invention, comprising: providing a plurality of recombinant M13 phages of the present invention, and allowing for self-alignment or applying an external force to align the plurality of recombinant M13 phages.

The invention having been described, the following examples are offered to illustrate the subject invention by way of illustration, not by way of limitation.

Example 1

Construction of Phage that Display Signaling Motifs

We developed a novel piezoelectric energy generating material using a bacterial virus, M13 phage. M13 phage possesses intrinsic piezoelectric properties due to the aligned dipole structure originating from the 2700 α-helical coat proteins along its long axis. We fabricated phage-based piezoelectric thin film materials and verified their chemical and physical structure-dependent piezoelectric properties. We could tune the piezoelectric strength of the phage through genetic engineering of the major coat protein by addition or deletion of negatively charged amino acid residues. Furthermore, stacked multi-layer phage films could enhance piezoelectric strength up to 7.8 pm/V. The resulting sandwiched phage film devices could produce up to 6 nA and 400 mV which is sufficient to operate a liquid crystal display device. Our novel biological electrical energy generating approach can be applied to many other similar biological materials and might provide a pathway to address demanding energy challenges without sacrificing carbon footprint.

Novel biopiezoelectric materials were fabricated by exploiting the naturally aligned dipole structure of a bacterial virus, M13 phage. Using piezoresponsive microscopy techniques, we characterized the structure-dependent piezoelectric properties of the phage at a molecular level. Furthermore, we enhanced the piezoelectric properties of phage through chemical and physical structure modification. Finally, we successfully demonstrated that a phage-based piezoelectric device could produce up to 6 nA and 400 mV. Our novel phage-based piezoelectric material presents an adaptable and cost-effective means of harvesting electric energy from the environment and is an important step toward accessing the largely untapped potential of piezoelectric biomaterials.

Figure 2:
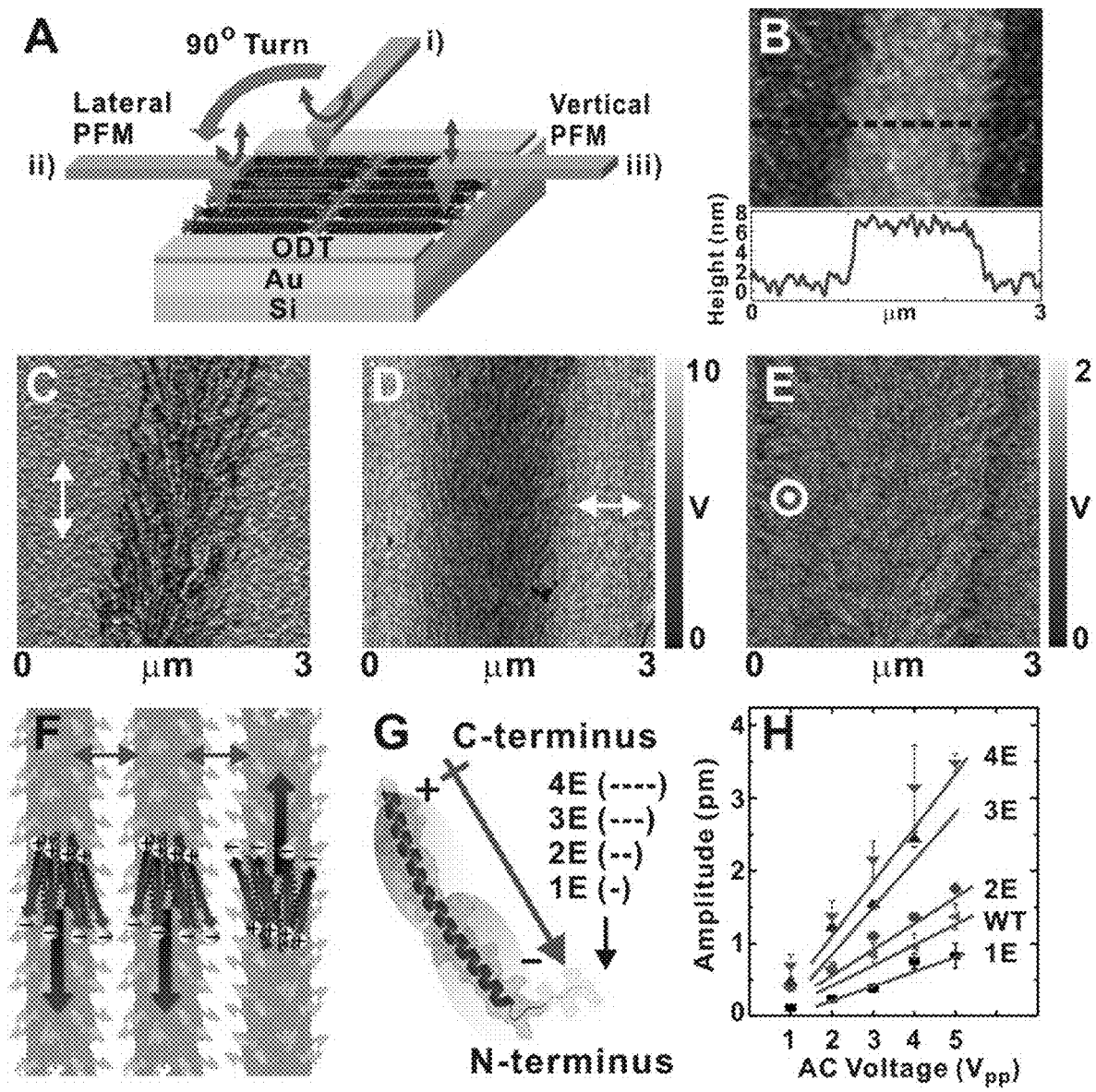
FIG. 2. Piezoelectric properties of phage monolayer films. (A) Schematic diagram of the piezoelectric response measurement. A single layer of phages was assembled on a molecularly patterned Au substrate and PFM responses were measured by lateral and vertical PFM modes. (B) AFM topography (top) and height profile (bottom) of single-layer phage film. (C) Lateral in-plane PFM image of the monolayer phage film. The lateral PFM signal is originated from the torsional motion of the AFM tip along the phage long axis direction as in (A, i). (D) Lateral in-plane PFM image obtained after changing the scanning direction by 90° from that of image as in (A, ii). The color scale corresponds to both (C) and (D). (E) Vertical out-of-plane PFM image of the monolayer phage film as in (A, iii). The vertical PFM signal is collected from the vertical motion of the AFM tip. (F) Schematic diagram depicting phage with randomly mixed dipoles through the axial direction of the monolayer, which exhibit both axial and radial components of dipole moments. (G) Schematic diagram of a single pVIII protein displaying varying numbers of glutamate at its N-terminus. (H) Comparison of out-of-plain PFM amplitudes between phages with genetically engineered coat-proteins. 1E-, wildtype-, 2E-, 3E-, and 4E-phage monolayer films exhibited effective piezoelectric coefficient $d_{eff}$ values of 0.19, 0.27, 0.31, 0.73, and 0.80 pm/V, respectively.

We first characterized the piezoelectric properties of the phage at a molecular level. Due to their well-defined shape and ability to display functional peptides through genetic and chemical modification, viral particles, including M13 phage, have previously been utilized to fabricate functional nanomaterials for inorganic nanomaterial synthesis and assembly (18-21), energy storage and generation (22-24), and tissue regeneration (25). Especially, M13 phage is a bacterial virus that has a long-rod shape (approximately 880 nm in length and 6.6 nm in diameter) (FIG. 1) (2, 17). It is covered by 2,700 copies of a major coat protein (pVIII) and five copies of minor coat proteins (pIII and pIX) located at either end. In addition, the major coat protein (pVIII) has an α-helical structure with a charged dipole from the carboxy- to amino-terminal direction, covering the phage body with five-fold rotational symmetry. Because the resulting aligned protein coat structure of M13 possesses neither a centrosymmetry nor an inversion center, we can expect that M13 phages possess piezoelectric properties. We verified the piezoelectric properties of the phage using piezoresponse force microscope (PFM), whereby the mechanical response of the material is monitored during the application of an electrical signal through a metal-coated AFM tip while scanning the sample (FIG. 2A) (26). In order to characterize the structure-dependent piezoelectric properties at the single phage level, we fabricated self-assembled phage monolayer films, patterned as 1 µm wide lines, on a Au substrate (27). AFM topography analysis (FIG. 2B) shows that the self-assembled films are composed of phage monolayers with a directionally ordered nematic structure ~7 nm in height, similar to the diameter of a single phage. The PFM characterization revealed that the piezoelectric phage responded to an applied electric field in both the lateral and axial directions (FIG. 2C-E). For lateral PFM, scanning along the phage long axis (FIG. 2C), the phage film exhibited characteristic bright and dark fibril textures. We believe that these fibril textures originate from the opposite directional piezoelectric responses of the randomly mixed up-and-down phage dipoles in the monolayer phage film (FIG. 2F). When we performed lateral PFM perpendicular to the phage long axis by rotating the sample 90°, the fibril texture contrast disappeared (FIG. 2D). This scanning direction-dependent piezoelectric contrast occurs because of the tilting angle (~21°) of the α-helical coat proteins with respect to the phage axis and the helical screw advancement (~41° pitch) of the dipole (FIG. 2F). This results in an axial component of the dipole whose sign is dependent on phage orientation and a radial component independent of orientation (27).

Having verified the inherent piezoelectric response of the phage fibers, we modulated the piezoelectric strength of the phage by engineering the pVIII coat protein through recombinant DNA techniques. Because we believe the coat protein dipole is induced mainly by the charge distribution of the pVIII coat proteins (i.e., the rich positively charged residues in the C-terminal region and rich negatively charged residues in the N-terminal region), we engineered the N-terminus of the pVIII major coat protein of the phage with different numbers of the negatively charged amino acid residue, glutamate, in order to modulate the piezoelectric strength of the phage (FIG. 2G). We created phages with varying numbers of glutamates (from one glutamate (1E) to four glutamates (4E)) inserted between the first (Ala) and fifth (Asp) amino acids of the pVIII major coat in the wildtype-phage. Since the wildtype-phage already contained two negative charges at the insert region (Glu(-)-Gly(0)-Asp (-)), 4E-phage displays two additional negative charges and 1E-phage displays one less negative charge than the wildtype-phage. Monolayer phage films were prepared with 1E-, 2E-, 3E- and 4E-phages as described earlier. These genetically engineered phage exhibited a chemical structure-dependent piezoelectric response (FIG. 2H). Vertical PFM measurements revealed that the effective piezoelectric coefficient ($d_{eff}$), calculated from the slope of the PFM amplitude versus the applied voltage curve, of the wildtype-phage was ~0.27 pm/V. We observed that the 1E-phage possessed the lowest $d_{eff}$ value of 0.19 pm/V followed by an increase in $d_{eff}$ for each additional negative charge up to the 4E-phage, which exhibited the highest value of 0.80 pm/V. The wildtype-phage exhibited a response similar to that of 2E-phage as expected based on their similar charge structures.

Figure 3:
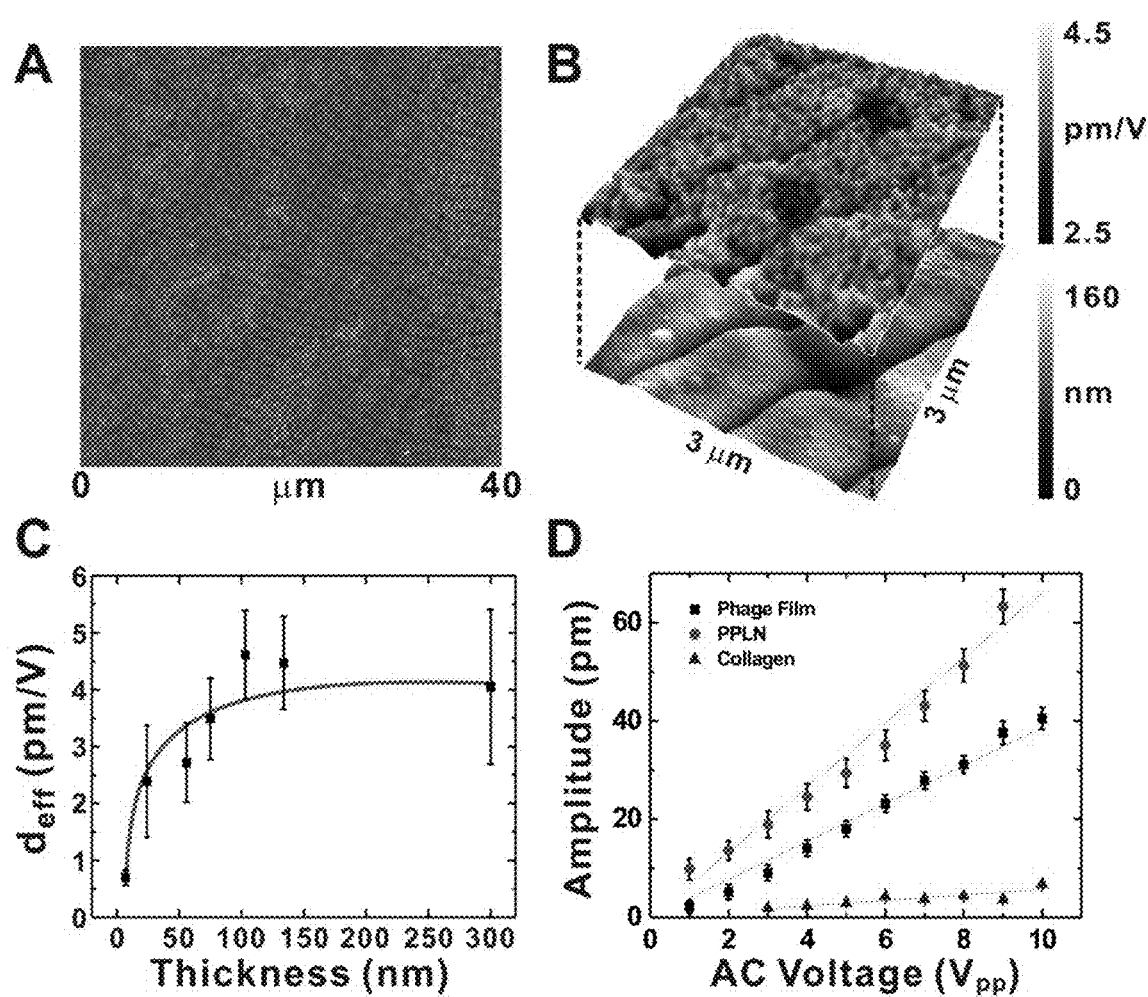
FIG. 3. Piezoelectric properties of phage multilayer films. (A) AFM topography image of the long range ordered smectic phase liquid crystalline thin film structure. (B) The effective piezoelectric coefficient $d_{eff}$ mapping image (top) and AFM topography image (bottom) of smectic phase ordered phage films. (C) The dependence of the piezoelectric response of 4E phage films on film thickness. (D) Comparison of the piezoresponse of phage films with those of periodically poled lithium niobate (PPLN) and collagen films. We obtained the effective piezoelectric coefficient $d_{33}$~7.8 pm/V for the phage film. For PPLN and collagen, $d_{33}$=13.2 pm/V and 0.9 pm/V, respectively.

The piezoelectric properties of the phage could be further enhanced by controlling the physical structure (i.e., thickness) of the phage films. We prepared multilayer phage films of varying thicknesses using the 4E-phage, which exhibited the largest response among the engineered phages (FIG. 2H). The AFM topography image (FIG. 3A) of the phage film showed that the film possessed a smectic liquid crystalline structure (ordered in both direction and position) with ~900 nm layer spacing (FIGS. 3A and B). The phage particles formed a ridge and groove band pattern, composed of the pVIII major coat proteins, and the pIII and pIX minor coat proteins, respectively. A piezoelectric coefficient mapping image (FIG. 3B) showed that $d_{eff}$ of the ridge areas is higher than that of the groove areas. Additionally, the observed piezoelectric response was dependent on the film thickness (FIG. 3C). The phage films exhibited an increased effective piezoelectric coefficient with increasing film thickness up to a saturated level of $d_{eff}$~3.9 pm/V for films greater than ~100 nm thick. Because the non-uniform electric field is applied to the sample through the AFM tip in our piezoelectric measurement, the relationship between $d_{eff}$ from the PFM measurements and the piezoelectric coefficient, $d_{33}$, is not straightforward (28). Previously, it has been reported that, in the weak indentation regime where the indentation of the AFM tip on the sample (~2 nm) is less than the tip radius (~10 nm), we can approximate the $d_{33}$ value by $d_{eff}=0.5d_{33}$ (26). Based on this relationship, we can estimate the actual $d_{33}$ value of the phage film to be 7.8 pm/V. Using the same piezoelectric measurement setup, we compared the piezoelectric response of the phage film with two control piezoelectric materials, type I collagen and periodically poled lithium niobate (PPLN) films. The measured $d_{33}$ values of collagen and PPLN were 0.9 and 13.2 pm/V, respectively (FIG. 3D), which is well-matched with previously reported values (12, 29). It should be noted that this rather low measured value for collagen arises because it displays a piezoelectric response mainly in the axial direction ($d_{31}$) rather than radially ($d_{33}$).

Figure 8:
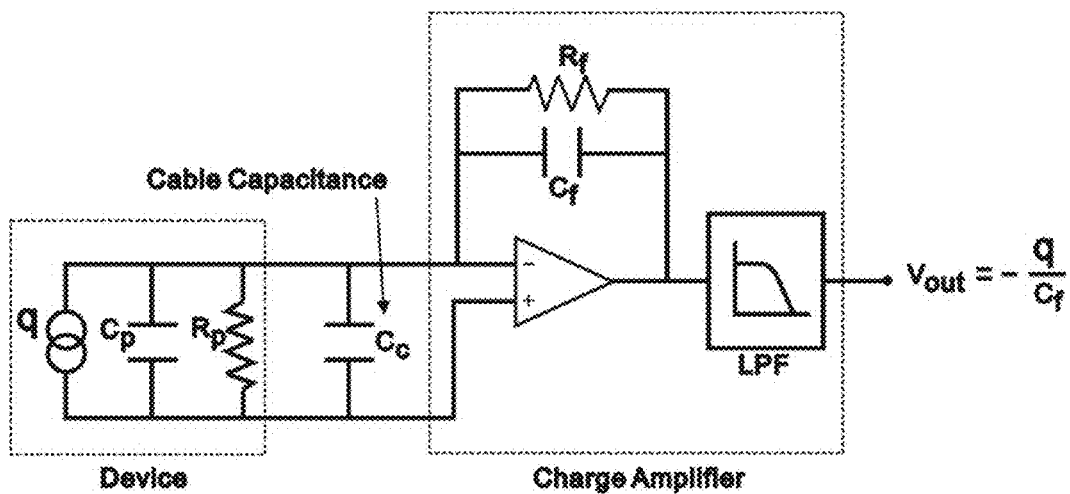
FIG. 8. Measurement setup diagram using charge amplifier. The device can be modeled as a charge source with a parallel capacitance ($C_p$) and resistance ($R_p$). The cable is modeled as parallel capacitance $C_c$. The charge amplifier converts the charge signal with high source impedance to a low impedance voltage output. The output voltage from the charge amplifier is only dependent on the input charge, q, and feedback capacitance, $C_f$ by the relationship $V_{out}=-q/C_f$. The charge amplifier also has a low-pass filter (LPF) stage to match the signal characteristics and reduce noise.
Figure 9:
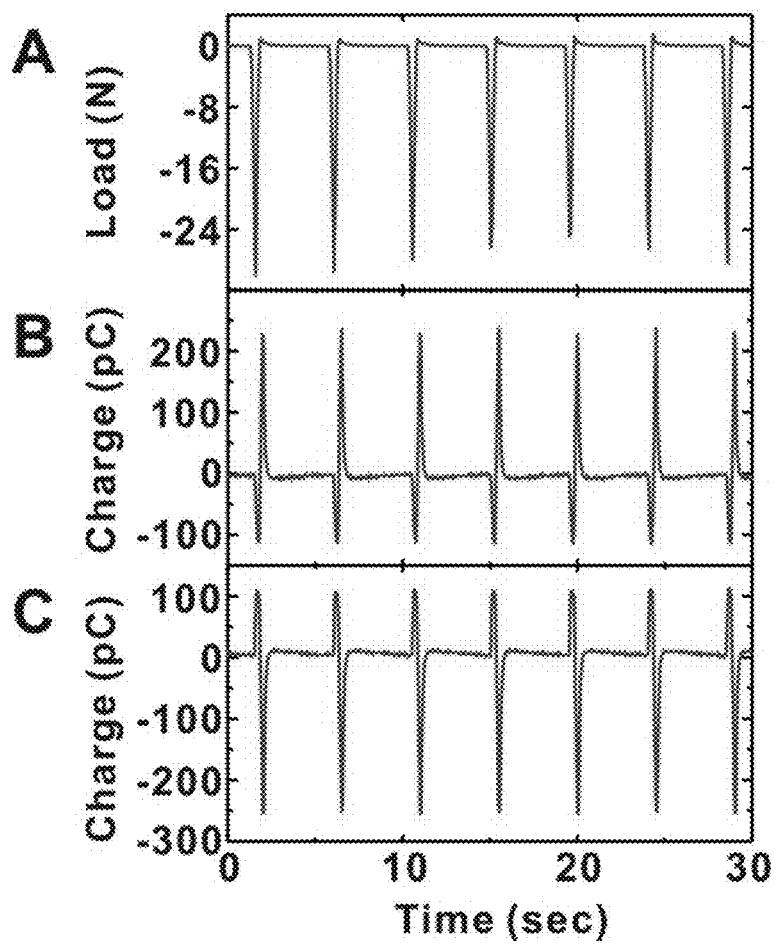
FIG. 9. Charge generation characterized by charge amplifier for periodic triangular load. (A) Typical load profile. The peak load value was ~130 N and the pushing and retrieving velocities were both 4 mm/sec. (B) Output signal from the charge amplifier. The output of the charge amplifier is a voltage signal which is converted into a charge value by multiplying by the total gain, 10 pC/V. (C) Connection polarity reversion test using the charge amplifier. The charge signal also showed polarity reversion with respect to (B) when the connection polarity of the amplifier to the device was reversed.
Figure 10:
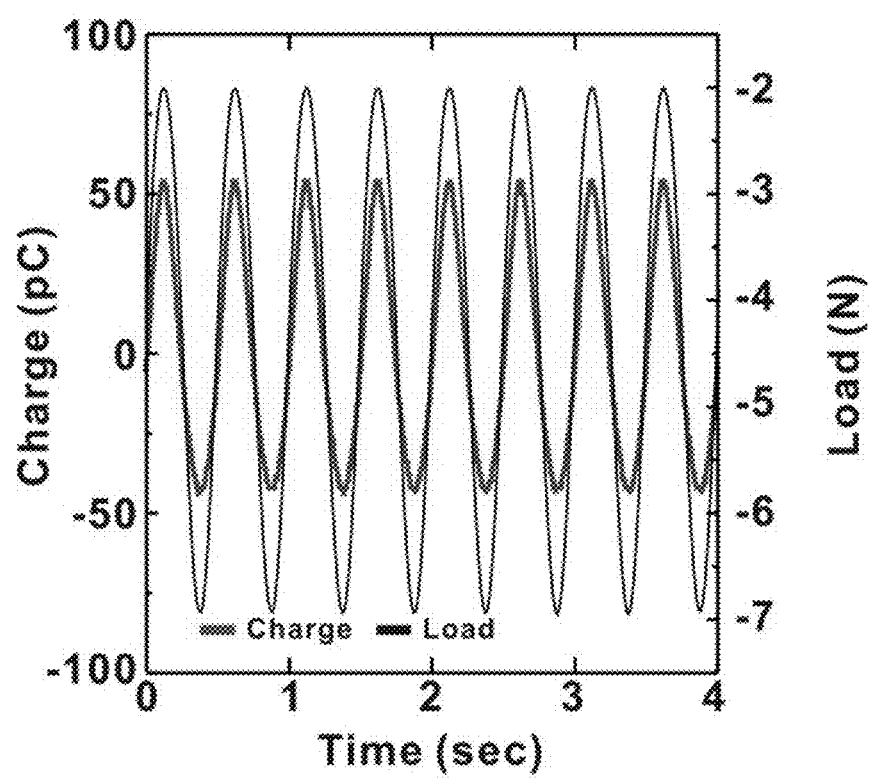
FIG. 10. Charge generation characterized by charge amplifier for periodic sinusoidal load. The charge signal also showed a sinusoidal response. A base compressive load of 3N is applied to assure good mechanical contact between the mechanical fixture and the device.

Using 4E-phage films, we fabricated phage-based piezoelectric energy generators. The phage-based generator consisted of a ~1 cm² multilayer phage film sandwiched between two metal electrodes (FIG. 4A). Periodic mechanical loads were applied to the phage-based piezoelectric generators using a dynamic mechanical test system and the resultant electrical signal output was characterized by measuring the short-circuit current, open-circuit voltage, and charge (FIG. 4B). When applying a rectangular compressive load (FIG. 4C) at 6 sec intervals, the signal showed two peaks of reverse polarity which corresponded to the pressing and releasing motion of the mechanical test system. From this experiment, we typically observed peak values of ~4 nA for the short-circuit current (FIG. 4D). This peak current level could be tuned by adjusting the strain and strain rate (FIG. 4F). The peak current increased linearly for strains from 0.06 to 0.1 and strain rates from 0 to 0.4 sec⁻¹. As a result, we were able to enhance the current output up to 6 nA. Furthermore, the integral of a single peak gives us the charge value, Q–393 pC, when a peak load of F=34 N was applied. Utilizing the equation for a quasi-static piezoelectric coefficient $d_{33}=Q/F$ (30), where Q and F are charge generated and applied load force, respectively, we can roughly estimate the piezoelectric coefficient as $d_{33}=11.6$ pC/N (pm/V), which is in close agreement with our proposed value of 7.8 pm/V. The open-circuit voltage shows a peak voltage value of 400 mV and a decay time constant of 0.3 sec. A connection polarity reversion test showed that the current and voltage signals were reversed when the device polarity was switched (5), indicating that the electrical signals came from the phage material and not from electrostatic interactions. We further confirmed that the piezoelectric energy generation originated only from the phage films by using a charge amplifier, which exhibited a similar charge output signal and reverse polarity (FIGS. 8 and 9). Additionally, by applying mechanical pressure to the phage-piezoelectric devices, we could power a liquid crystal display (Movie S1; and detail procedures are available in the Supplementary Information of Lee, et al. "Virus-based piezoelectric energy generation," Nature Nanotechnol. 7:351-356 (2012), which are incorporated by reference). As such, we have confirmed that these natural viral particles effectively behave as piezoelectric nanofibers with the potential for powering microelectronic devices.

In summary, we have developed a piezoelectric energy converting biomaterial from a self-replicating bacterial virus, M13 phage. We verified the chemical and physical structure-dependent biopiezoelectric properties of the phage using piezoresponsive microscopy techniques and fabricated piezoelectric generators to produce electrical energy up to 6 nA and 400 mV. Future improvement of our phage-based energy generator will be the development of parallel connected devices to achieve high electric energy output and the combination of microfabricated electrodes and self-assembly of phage thin films to improve efficiency. Additional modifications to enhance phage dipole strength, such as chemical modification or inorganic dopant incorporation will be developed. In addition, because there are many different types of viral particles and proteins (i.e, microtubules, membrane proteins) which possess distinctly aligned dipoles, our demonstrated approach opens the door to utilizing this many class of biomaterials to create novel biopiezoelectric generators. As a result, we believe the development of our phage-based piezoelectric nanofibril material, could play an important role in addressing future energy challenges.

Materials and Methods

Construction of the Engineered Phages

We constructed engineered phages using recombinant DNA engineering methods (25, 31). The desired peptides (Table 2) were expressed at the N-terminus of the M13 major coat protein, positioned between the first and fifth amino acids of wildtype pVIII, replacing residues 2-4 (Ala-Glu-Gly-Asp-Asp with Ala-(Insert)-Asp) (SEQ ID NO:3). To facilitate recircularization of the engineered plasmid, a Pst I restriction site (CTGCAG) (SEQ ID NO:4) was created by mutating the nucleic acid at position 1372 of the M13KE vector (NEBiolabs, Ipswich, MA, USA) from T to A by site directed mutagenesis (QuickChange® Kit, Stratagene, La Jolla, CA, USA). Following mutagenesis, the DNA sequence was verified by standard microbiological methods (3). To create pVIII insertions, primers (p8-1E~p8-4E) were designed and ordered (IDT, Coralville, IA, USA). (Table 2) A linearization primer (p8-rev1376) was also created. To incorporate the gene sequences, polymerase chain reaction (PCR) was performed using Phusion™ High-Fidelity DNA polymerase (Finnzymes, Espoo, Finland), two primers (insert and linearization), and the M13KE vector with the engineered PstI site as the template. The product was separated on an agarose gel, purified on a spin column, digested with PstI enzyme (NEBiolabs, Ipswich, MA, USA), and recircularized overnight at 16° C. with T4 DNA Ligase (NEBiolabs, Ipswich, MA, USA) (3). The ligated DNA vector was transformed into XL1-Blue electroporation competent bacteria (Stratagene, La Jolla, CA, USA), and the sequences of the products were verified via DNA sequencing at the University of California, Berkeley DNA sequencing facility. The constructed phage was amplified using *E. coli* cultures, purified using polyethylene glycol precipitation, and filtered through 0.45 μm pore size membranes. To verify phage stability, DNA sequences were confirmed at each step of the amplification.

TABLE 2

Primer sequences for pVIII engineering

| Name | Oligonucleotide Primer Sequence* | Insert Peptide Sequence** |
|---|---|---|
| p8-1E | 5'ATATATCTGCAG*CTGCAGAGGGC*GACCCCGCAAAA GCGGCC 3' (SEQ ID NO: 5) | A*EGD*P (SEQ ID NO: 10) |
| p8-2E | 5'ATATATCTGCAG*CTGCAGAGGAGGGC*GACCCCGCA AAAGCGGCC 3' (SEQ ID NO: 6) | A*EEGD*P (SEQ ID NO: 11) |
| p8-3E | 5'ATATATCTGCAG*CTGCAGAGGAAGAGGGC*GACCCC GCAAAAGCGGCC 3' (SEQ ID NO: 7) | A*EEEGD*P (SEQ ID NO: 12) |
| p8-4E | 5'ATATATCTGCAG*CTGCAGAGGAAGAGGAG*GACCCCG CAAAAGCGGCC 3' (SEQ ID NO: 8) | A*EEEED*P (SEQ ID NO: 13) |
| P8-rev1376 | 5' CCTCTGCAGCGAAAGACAGCATCGG 3' (SEQ ID NO: 9) | |

*For primer oligonucleotide sequences the restriction sites are shown in bold, and the insert is underlined and in italic.
**For the resulting peptide sequence the insert is underlined and in italic. Here, A, E, G, D, P stands for Alanine, Glutamate, Glycine, Aspartate, and Proline, respectively. In the insert peptide sequence, E has one negative charge, and G has no charge.

Fabrication of Monolayer Phage Films

Using a polydimethylsiloxane (PDMS) stamp with a striped pattern, 2 μm wide lines of an octadecanethiol (ODT) self-assembled monolayer with 1 μm inter-line spacing were formed on a Au-coated Si substrate (100 nm Au layer over 5 nm Ti adhesion layer) (Platypus Technologies, Madison, WI, USA). After thorough washing with ethanol and $N_2$ blow drying, the remaining area on the substrate was backfilled with cysteamine in 3 mM aqueous cysteamine solution for 2 min. The resulting ODT/cysteamine pattern substrate was washed with DI water and ethanol, blow-dried with $N_2$ gas, and immediately used for phage pattern formation. A monolayer of phage was coated onto the cysteamine pattern using a dip-coating method. The ODT/cysteamine patterned substrate (having a vertical cysteamine stripe pattern) was vertically dipped into a phage solution (1 mg/mL in deionized water) and pulled out at a constant speed (1.2 cm/h) using a home-built machine controlled by a computer-programmed system (4). The phage patterned substrate was air dried for 2 h and kept in a desiccator prior to use.

Multilayer Phage Film Fabrication

Multilayer phage films were prepared with either the pulling method or the drop-cast method. By the pulling method, we obtained multilayer phage films of thickness up to ~300 nm. For liquid crystalline phage films with thicknesses higher than 300 nm, we utilized the drop-cast method. In this case, 100 μL of phage solution (2 mg/mL in DI water) were dropped onto an Au substrate and kept in a desiccator for 3 days. The resulting phage film exhibited regions of smectic phase with highly ordered and well packed phages.

Piezoelectric Response Characterization of Monolayer Phage Films

For the qualitative vertical and lateral PFM characterization of the single layer phage films, we utilized a AFM setup (Multimode, Veeco, Plainview, NY, USA) with a NANOSCOPE IV™ controller. We noted that the usage of a metal-coated AFM tip with a low spring constant results in maximum PFM contrast. We used a TR400PB™ (Olympus, Tokyo, Japan) Au-coated tip with a spring constant of ~0.1 nN/nm. The usual force applied to the sample during PFM measurements was ~1 nN, which corresponds to a ~0.4 nm indentation, as determined by the force-distance curve. PFM measurements were performed under ambient conditions. A driving AC voltage of 4 $V_{pp}$ at 6.39 kHz was applied to the tip. The piezoresponse amplitude and phase signals were monitored while scanning the AFM tip on the sample surface. When a mechanical motion in response to the electric field was detected on the quadrant photodetector of the AFM, the vertical and lateral signals were directed to separate lockin amplifiers. In the lockin amplifier, the input signal was multiplied by zero-phase and 90°-phase reference signals and lowpass filtered to obtain the in-phase ($S_I$) and quadrature phase ($S_Q$) signals. The FIGS. 2 (C), (D), and (E) show the in-phase signal, A×sin (phase), where A= $(S_I^2+S_Q^2)^{1/2}$ is the vertical or lateral amplitude signal from the quadrant photodetector of the AFM.

Piezoelectric Response Characterization of Multilayer Phage Films

Figure 5:
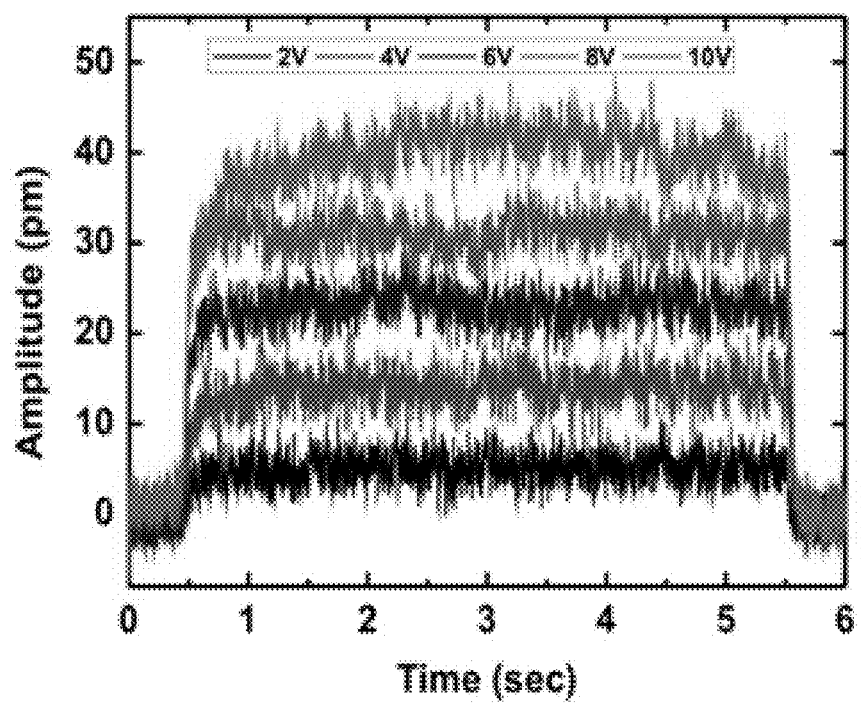
FIG. 5. Real-time PFM signal on 4E-phage film. The sample was characterized by creating a force map on the sample in which an AC signal with amplitudes from 1 to 10 V was applied at 1V intervals for 5 sec before moving to the next point. In this graph, we show only the signals for 2, 4, 6, 8, 10 V to avoid cluttering. The effective piezoelectric coefficient, $d_{eff}$, was determined by plotting the average amplitude versus the applied voltage amplitude and obtaining the slope by linear fitting.
Figure 6:
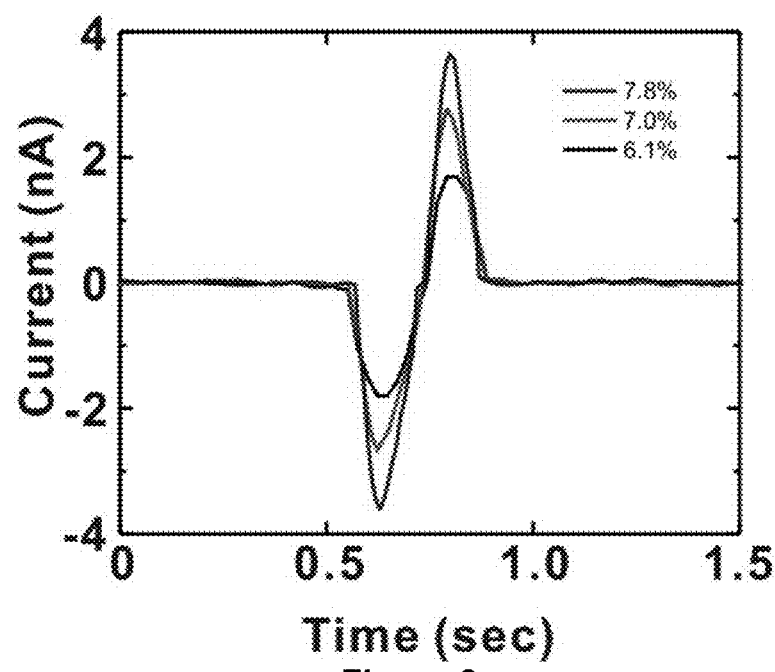
FIG. 6. Peak current dependence on strain. Three curves are shown corresponding to strains of 6.1%, 7.0%, 7.8%. Strain is defined as the ratio of the compressive displacement of the sample (ΔL) to the initial thickness of the sample ($L_0$).
Figure 7:
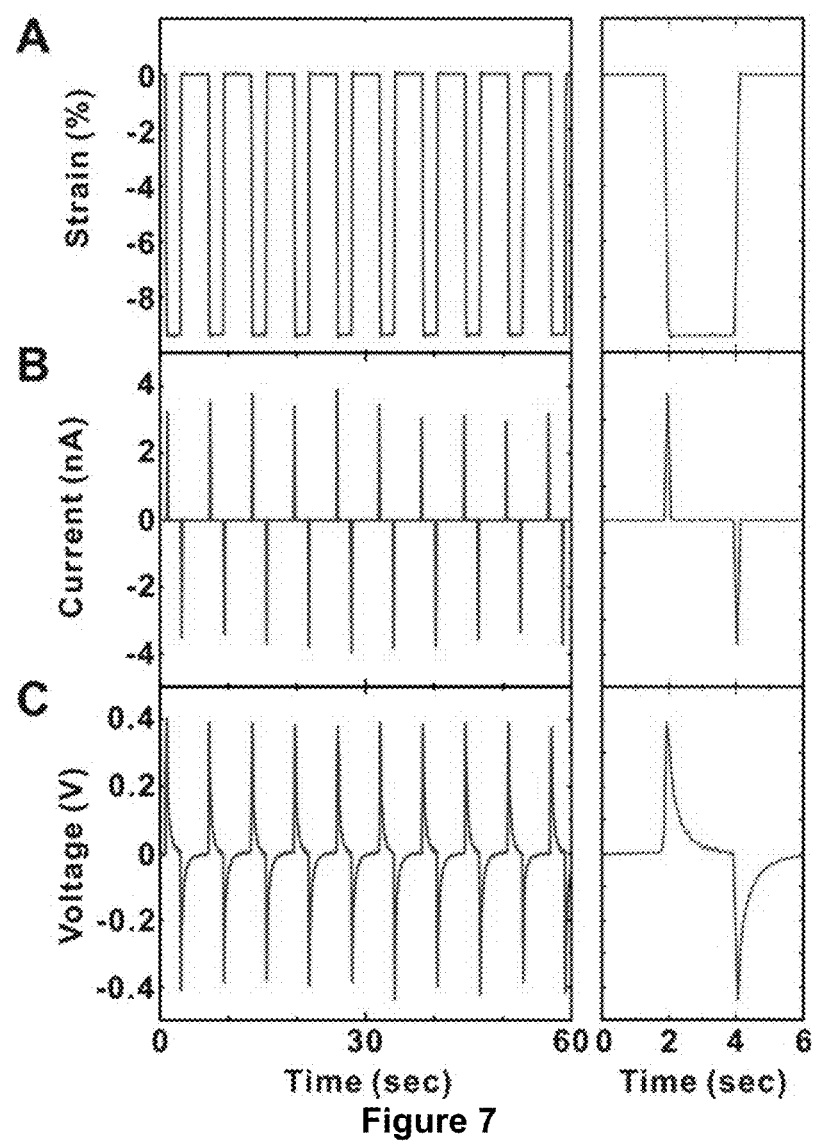
FIG. 7. Characterization of phage-based piezoelectric energy generator with connection polarity reversion setup. (A) Applied mechanical strain onto the device. (B) Short-circuit current signal and (C) open-circuit voltage signal from the phage-based generator.

For the quantitative determination of the vertical piezoelectric coefficient $d_{33}$, we utilized a MFP-3D™ AFM (Asylum Research, Santa Barbara, CA, USA) with a Pt-coated AC240TS™ (Olympus, Tokyo, Japan) tip with a spring constant of ~2 nN/nm and a free-air resonance frequency of ~70 kHz. Measurements were performed under ambient conditions. The usual force applied to the sample during PFM measurements was ~100 nN, which corresponded to a ~2 nm indentation as determined by the force-distance curve. A driving AC voltage of peak-to-peak voltage from 1V to 10V was applied to the tip (FIG. 5).

For determination of the AC signal frequency, the contact resonance frequency was first determined by bringing the tip into contact with the sample and sweeping the frequency while monitoring the amplitude. The typical contact resonance frequency value was ~280 kHz. Afterward, the AC driving frequency (usually ~20-40 kHz) was chosen so that the driving frequency was far enough away from the contact resonance frequency that the piezoresponse amplitude was independent of the driving frequency. When a mechanical motion in response to the electric field was detected on the quadrant photodetector of the AFM, the vertical signal was directed to an internal lockin amplifier in the AFM controller. In the lockin amplifier, the input signal was multiplied by zero-phase and 90°-phase reference signals and lowpass filtered to obtain the in-phase ($S_I$) and quadrature phase ($S_Q$) signals. The amplitude signal A=$(S_I^2+S_Q^2)^{1/2}$ was measured and then averaged to determine the amplitude at the specific driving voltage.

Phage-Based Generator Fabrication

Figure 4:
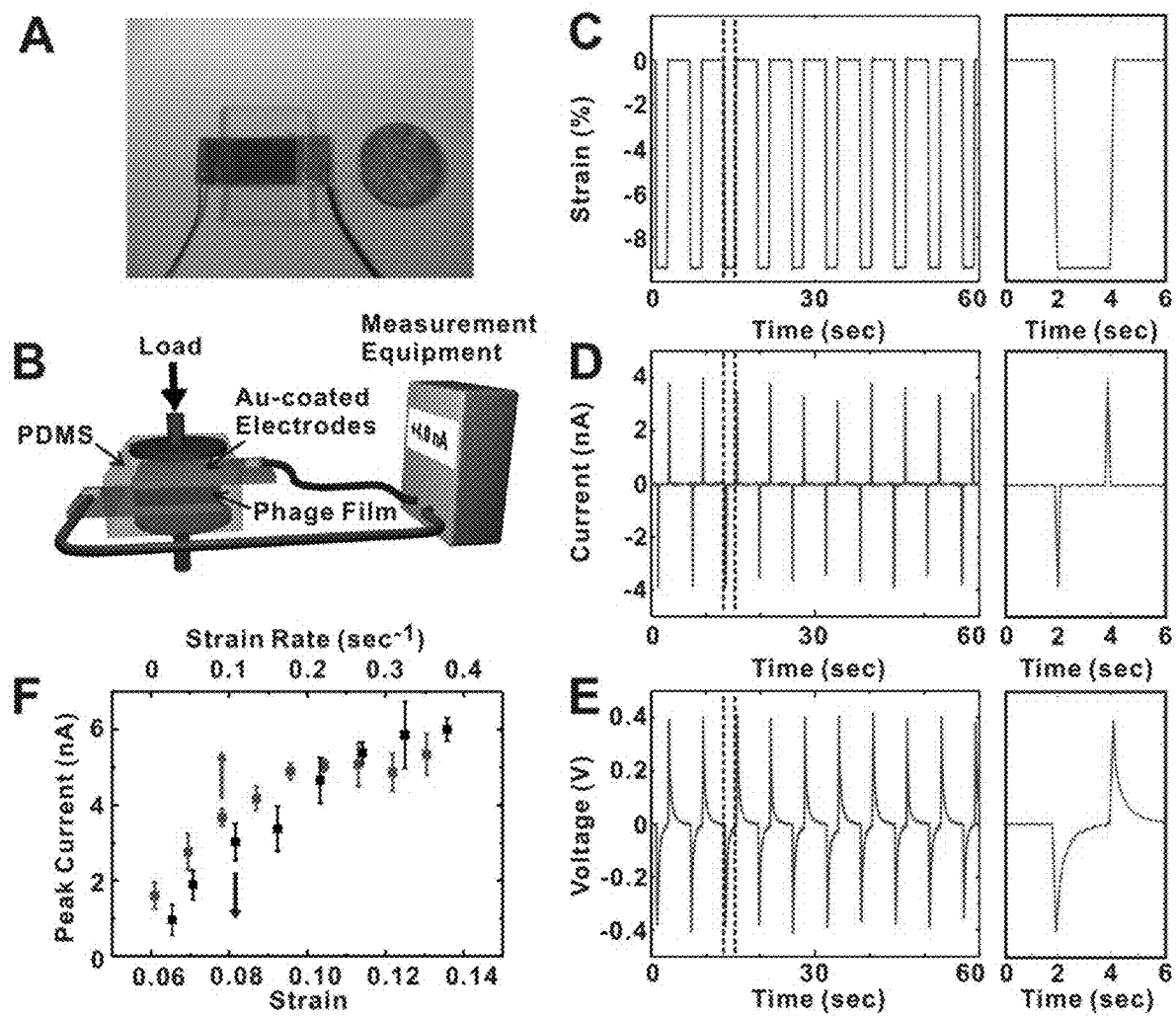
FIG. 4. Characterization of phage-based piezoelectric energy generator. (A) Photograph of a phage-based generator. (B) Schematic diagram of the piezoelectric electric energy generation measurement setup. A mechanical load was applied to the device while monitoring the voltage and current. (C) Applied mechanical strain onto the device, (D) short-circuit current signal, and (E) open-circuit voltage signal from the phage-based generator. The two vertical dotted lines highlight the instance of pressing (left line) and releasing (right line) of the load. (F) Dependence of the phage-based generator peak current amplitude on strain and strain rate. Strain is defined as the ratio of the device vertical displacement to the initial device thickness.

Gold-coated flexible substrates were prepared by depositing 10 nm Cr and 30 nm Au on THERMANOX™ films. Then, 200 μL of 5 mg/mL 4E-phage solution were dropped on the gold-coated flexible substrate. The solution was air dried, during which the phages formed highly-ordered smectic regions and showed large area ordered structures. After drying, another gold-coated flexible substrate was overlaid on the film. The effective device area, where the phage films and electrodes overlap, was ~1 cm². The device was then embedded between two ~2.5 mm thick PDMS films for structural stability (FIG. 4). Lastly, signal wires were soldered onto the gold electrodes.

Measurement of the Device Impedance

As described herein, the phage-based generator consists of a phage film placed between two gold electrodes. Therefore, the device can be modeled as a charge generator with a parallel resistor $R_p$ and capacitor $C_p$ (FIG. 8). The capacitance was measured using an LCR meter (4285A, Agilent Technologies, Santa Clara, CA, USA). All of the devices had a ~1 cm² phage film area and the thickness of the phage film made with the drop-cast method was ~10 μm. The estimated value of the capacitance, using the ideal capacitor model, can be calculated as $$C = \frac{\varepsilon_r \varepsilon_0 A}{d},$$

where $\varepsilon_r$ is the dielectric constant, $\varepsilon_0$ is the free space permittivity ($\varepsilon_0$=8.85×10⁻¹² F/m), d is the distance between two electrodes, and A is the area of the capacitor. Using the values $\varepsilon_r$=3 (taking the nominal value from reference (5)), A=1 cm², and d=10 μm, we obtain C≈265 pC. The measured values of the parallel capacitance by the LCR meter for 10 devices was $C_p$≈63±21 pC, with the difference presumably coming from the differences in dielectric constant, film thickness, and non-ideality in the capacitor model.

The resistance was measured separately with a semiconductor parameter analyzer (4200-SCS, Keithley, OH, USA) because the resistance value was beyond the measurable limits of the LCR meter. IV curve measurements were performed for each device from which the resistance values were determined from the inverse of the slopes. The current noise level of the semiconductor analyzer was ~1 pA during the IV curve measurements. The IV curves showed linearity, validating modeling the device as a parallel capacitor and resistance. The resistance values measured were $R_p$≈4.9±2.6 GΩ.

Phage-Based Piezoelectric Generator Characterization

The entire device was mounted onto a dynamic mechanical test system (Electroforce 3200, Bose, MN, USA) and a predefined displacement was applied while monitoring the total force on the device with a load cell. The actual displacement was monitored by a linear variable differential transformer (LVDT) installed in the ELECTROFORCE 3200™ test system. The force values from the load cell were multiplied by the ratio of the phage film area to the total device area to obtain the effective load applied to the phage film.

In our experiment, we measured both current/voltage signals and charge. To measure the open circuit voltage of the phage-based generator, a semiconductor parameter analyzer (4200-SCS, Keithley, OH, USA) was used in zero-current (I=0) mode. In this mode, the observed current level was less than ~1.5 pA during the measurement. To measure the short circuit current of the phage-based generator, the semiconductor parameter analyzer was used in zero-voltage (V=0) mode. In this mode, the observed voltage level was less than ~1.0 μV during the measurement.

Charge Measurement Using Charge Amplifier

We characterized the charge generation from the phage-based piezoelectric devices. Since our device has a large source impedance, voltage measurements can be affected by the cable capacitance, stray capacitance, and input impedance of the measurement equipment. Also, the voltage measurement can be influenced by the small change in the sample capacitance, $C_p$, resulting from the mechanical load. To minimize these effects, we measured our signals using a charge amplifier (FIG. 8) (34). The utilization of a charge amplifier on the piezoelectric device provides the advantage of eliminating the effect of the capacitance from the sample, cables, and the measurement equipment. Due to the large open-circuit gain of the amplifier, the effects of the parasitic capacitance are suppressed. Also, since the charge amplifier only measures the charge, the effect of the capacitance change of the device by the mechanical force applied is minimized. In our experiment, a charge amplifier (Type 2626 Conditioning Amplifier, Bruel & Kjaer, Denmark) was used with coaxial cabling. The cables near the device were secured and clamped to ensure there were no triboelectric effects, as suggested by the manufacturer. The input and output sensitivities were selected at a range such that the amplifier showed no overload and had a high enough signal-to-noise ratio. The output port of the charge amplifier acts as a low impedance voltage source and, therefore, the output voltage from the amplifier was measured and recorded with an oscilloscope (TDS 1001B, Tektronix, OR, USA) with 1 MΩ input impedance. The output of the charge amplifier is measured in voltage, which is converted to units of charge (pC) by multiplying the voltage value with the total gain G [pC/V], obtained from the input sensitivity $S_{in}$ [pC/g] and output sensitivity $S_{out}$ [V/g] by the relationship $G=S_{in}/S_{out}$. Here, g is the standard gravity (9.8 m/s²), used as the unit of acceleration. Also, the charge amplifier provides bandpass filtering by controlling the low-pass ($f_L$) and high-pass cutoff frequencies ($f_H$). The low-pass cutoff frequency $f_L$ is determined by the feedback resistance ($R_f$) and capacitance ($C_f$) by the relationship $f_L=1/(2\pi R_f C_f)$. The low-pass cutoff frequency should be low enough not to affect the signal from the device. This also means that the time constant of the amplifier ($R_f C_f$) should be larger than the source time constant ($R_p C_p$). In our experiment, the amplifier settings were $S_{in}=1.0$ pC/g, $S_{out}=0.1$ V/g, $f_L=3$ Hz, $f_H=300$ Hz. After placing our sample in the dynamic mechanical measurement system, we applied triangular and sinusoidal loads.

Powering a Liquid Crystal Display

We were able to power up a liquid crystal display (LCD), showing similar device behavior as reported by Hu et al (8). The LCD was taken from a laboratory timer (TRACEABLE® 4-channel timer, Fisher Scientific, Waltham, MA, USA), and two pins were selected so that the number "1" would be displayed on the LCD. Two thin copper wires were attached to the pins using silver paint (SPI Supplies, West Chester, PA, USA) and then connected to the device wires using alligator clips. When we applied a periodic mechanical stimulus using the ELECTROFORCE 3200™ test system, we were also able to continuously display the number "1". One major difference that we noted from Hu et al is that the displayed image showed a much longer decay time (~1~2 sec), presumably due to the larger sample resistance of our devices (~4.9 GΩ) compared to that reported by Hu et al (~5.3~66.7 MΩ). The powering of the LCD, followed by the decaying of the displayed number when the mechanical stimulus was turned off was filmed.

References Cited:

1. P. Rakbamrung et al., *Sens. Actuators, A Phys.* 163, 493 (2010).
2. D. A. Marvin, L. C. Welsh, M. F. Symmons, W. R. P. Scott, S. K. Straus, *J. Mol. Biol.* 355, 294 (2006).
3. M. A. Galhardi, T. H. Guilherme, V. L. Junior, *7th Brazilian Conference on Dynamics, Control and Applications*, (2008).
4. Z. L. Wang, J. Song, *Science* 312, 242 (2006).
5. S. Xu et al., *Nat. Nanotechnol.* 5, 366 (2010).
6. Y. Qin, X. D. Wang, Z. L. Wang, *Nature* 451, 809 (2008).
7. X. Chen, S. Y. Xu, N. Yao, Y. Shi, *Nano Lett.* 10, 2133 (2010).
8. Y. Hu, Y. Zhang, C. Xu, G. Zhu, Z. L. Wang, *Nano Lett.* 10, 5025 (2010).
9. G. Zhu, R. Yang, S. Wang, Z. L. Wang, *Nano Lett.* 10, 3151 (2010).
10. C. Chang, V. H. Tran, J. Wang, Y.-K. Fuh, L. Lin, *Nano Lett.* 10, 726 (2010).
11. Y. Saito et al., *Nature* 432, 84 (2004).
12. M. Minary-Jolandan, M. F. Yu, *Nanotechnology* 20, 6 (2009).
13. A. A. Marino, J. A. Spadaro, E. Fukada, L. D. Kahn, R. O. Becker, *Calcif. Tissue Int.* 31, 257 (1980).
14. E. Fukada. (Ieee-Inst Electrical Electronics Engineers Inc, 2006), pp. 1110-1119.
15. E. Korostoff, *J. Biomech.* 10, 41 (1977).
16. J. L. F. Weytjens, D. A. Viberg, A. A. Caputi, K. Kallesoe, J. A. Hoffer, *J. Neurosci. Methods* 45, 217 (1992).
17. D. Rodi, S. Mandava, L. Makowski, in *Phage Display In Biotechnology and Drug Discovery*. (CRC Press, 2005), pp. 1-61.
18. S.-W. Lee, C. Mao, C. E. Flynn, A. M. Belcher, *Science* 296, 892 (2002).
19. C. B. Mao et al., *Science* 303, 213 (2004).
20. M. T. Klem, M. Young, T. Douglas, *J. Mater. Chem.* 18, 3821 (2008).
21. D. M. Kuncicky, R. R. Naik, O. D. Velev, *Small* 2, 1462 (2006).
22. Y. J. Lee et al., *Science* 324, 1051 (2009).
23. K. T. Nam et al., *Science* 312, 885 (2006).
24. K. T. Nam et al., *Proc. Natl. Acad. Sci. U.S.A* 105, 17227 (2008).
25. A. Merzlyak, S. Indrakanti, S. W. Lee, *Nano Lett.* 9, 846 (2009).
26. S. V. Kalinin, D. A. Bonnell, *Phys. Rev. B* 65, 125408 (2002).
27. S. Y. Yoo, W.-J. Chung, T. H. Kim, M. Le, S.-W. Lee, *Soft Matter* 7, 363 (2011).
28. C. Durkan, M. E. Welland, D. P. Chu, P. Migliorato, *Phys. Rev. B* 60, 16198 (1999).
29. T. Jungk, A. Hoffmann, E. Soergel, *New J. Phys.* 11, (2009).
30. IEEE, *IEEE Standard on Piezoelectricity*-1987. (1987).
31. A. Merzlyak, S.-W. Lee, *Bioconjugate Chem.* 20, 2300 (2009).
32. J. Sambrook, D. W. Russell, *Molecular Cloning: A Laboratory Manual*. (CSHL Press, ed. 3rd, 2001).

33. M. K. Gilson, B. H. Honig, *Biopolymers* 25, 2097 (1986).
34. Z. Wang, J. Hu, A. P. Suryavanshi, K. Yum, M.-F. Yu, *Nano Lett.* 7, 2966 (2007).

The references cited are incorporated by reference herein.

Example 2

Multi-Dimensional Micro-Patterning Through Self-Templating Material Assembly

Precisely defined multi-dimensional hierarchical structures in nano- or micrometer scale are a requisite for the fabrication of various functional devices in all fields of science and engineering. Conventional lithography techniques (i.e., photolithography, e-beam lithography, dip-pen nanolithography, nanoimprint lithography, and etc.) have been utilized to fabricate various devices for electronics, mechanics, and biomedical engineering. Despite their remarkable attributes and capabilities, those fabrication processes often require complicated procedures as well as considerable labors and expenses. However, in nature many hierarchically organized nanostructures (i.e., diatoms, abalone shell, butterfly wing, and moth eyes) possess exquisite structures and functions, which surpassing the capability achievable by current top-down and bottom-up fabrication methods. Moreover, many of these structures are made of a simple basic building block, helical nanofiber (i.e., collagen for animals and cellulose for plants) through self-templated assembly processes.

Inspired by nature's self-templated assembly processes, a novel biomimetic micropatterning technique is developed to create well-defined two- and three-dimensional hierarchical structures by controlling surface tension force of helical nanofiber particles at the air/liquid/solid interfaces. M13 bacteriophage (phage) is utilized as a model helical nanofiber building block, due to its' monodispersity, liquid crystalline property, and genetic flexibility to display functional peptides. By controlling meniscus forces, one can induce formation of the smectic nanofilament phases of the phage and tune the adhesion properties between the nanofilaments-to-nanofilament and nanofilament-to-solid substrates. The resulting structures possess hierarchically organized two- and three-dimensional periodic structures with exquisite optical properties. These self-assembled multi-dimensional hierarchical structures are tunable by varying parameters that affect the kinetics and thermodynamics of assembly such as pulling speed, pulling time, surface charges of phages, and ionic concentration. The resulting microstructures can enhance the power of phage-based piezoelectric energy generations. This bio-inspired self-assembly strategy provides a way to fabricate large-scale advanced micro electronic or optical devices and biomedical applications.

The M13 bacteriophage (virus), which is composed of a single-stranded DNA encapsulated by various major and minor coat proteins, is utilized to prepare hierarchical structures. It has a long-rod filament shape that is approximately 880 nm long and 6.6 nm wide. The major coat protein pVIII has an alpha-helical structure that possesses a dipole aligned structure in the C-terminal to N-terminal direction. Through genetic modification, functional peptides can be displayed on the pIII and pIX minor coat proteins and the pVIII major coat protein. These peculiar features of M13 bacteriophages can be available to form various liquid crystalline structures, such as nematic, cholesteric, and smetic structures. Engineered phages with two (EE), three (EEE), four (EEEE) (SEQ ID NO:2) glutamic acids on their pVIII major coat protein are used to increase surface charges of the phages.

Figure 11:
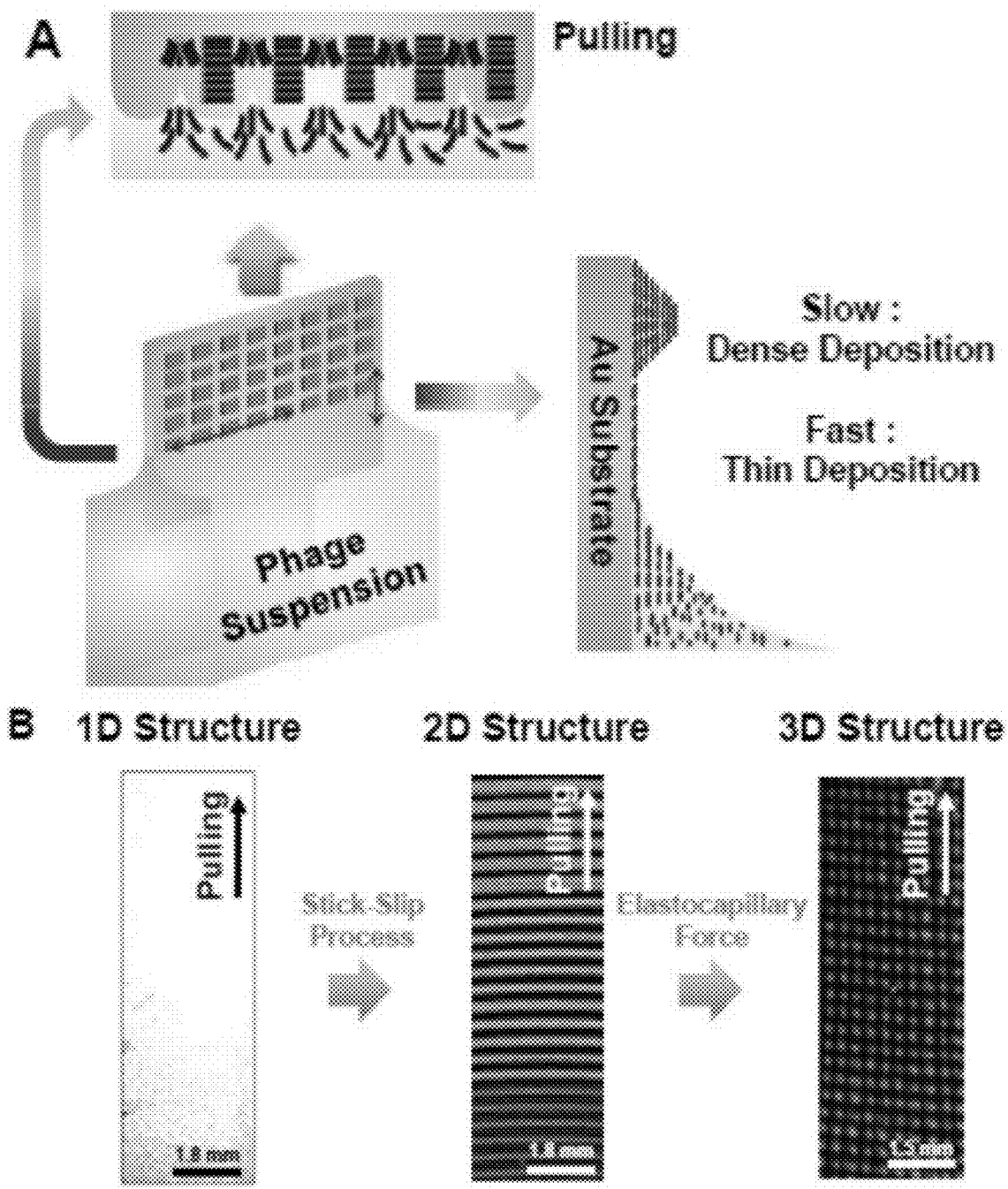
FIG. 11. Novel micropatterning technique to create two- and three-dimensional hierarchical structures by controlling coalescence of helical nanofiber particles with meniscus forces. (A) Schematic diagram illustrating meniscus force driven self-assembly of M13 phages for fabricating multi-dimensional hierarchical structures. (B) Optical images showing 1D, 2D, and 3D hierarchical structures prepared by this novel self-assembly method.

Self-assembled multi-dimensional microscale patterns are formed using meniscus driven thin film growth process through the control of the kinetic and thermodynamic parameters at the air/liquid/solid interfaces, as depicted in FIG. 11. Using a computer-controlled pulling apparatus, a substrate is pulled vertically from phage suspensions at precisely controlled speeds and times. Varying concentration of the phage solutions are prepared ~1 mg of 4E-phage pellet homogeneously suspended in 1 ml of in various ionic concentration in the uM to mM range. Silicon (100) wafers coated with gold (~0.5 cm×1 cm) will be placed in the viral suspension and pulled vertically at precisely controlled alternating speed (fast and slow; Fast=3 mm/m for 1.5 sec and Slow=10 μm/h for 600 sec pulling, repeatedly). As the substrates are pulled, evaporation proceeded fastest near the air-liquid-solid contact line resulting in the local accumulation and deposition of phage particles on the substrate at the meniscus. By controlling meniscus forces, one can induce formation of phage bundles and tune the adhesion between the bundles-to-bundles and bundles-to-substrates. In a certain range of ionic concentration, one can develop continuous line patterns that stick to the substrates. In lower than a critical ionic concentration, the deposited phage suspensions in continuous meniscus line at the water-substrate interface tend to segregate into periodically distributed domains to form the regular micro patterns due to the competing interfacing forces (fingering instability). These microscale patterns are continuous developed for form and one can fabricate multi-dimensional hierarchical structures composed of cholesteric-like phase of the nanofilaments (that is, smectic phage structures). Through control of the kinetic and thermodynamic forces, one can control the horizontal and vertical pattern spacing and their height.

Figure 12:
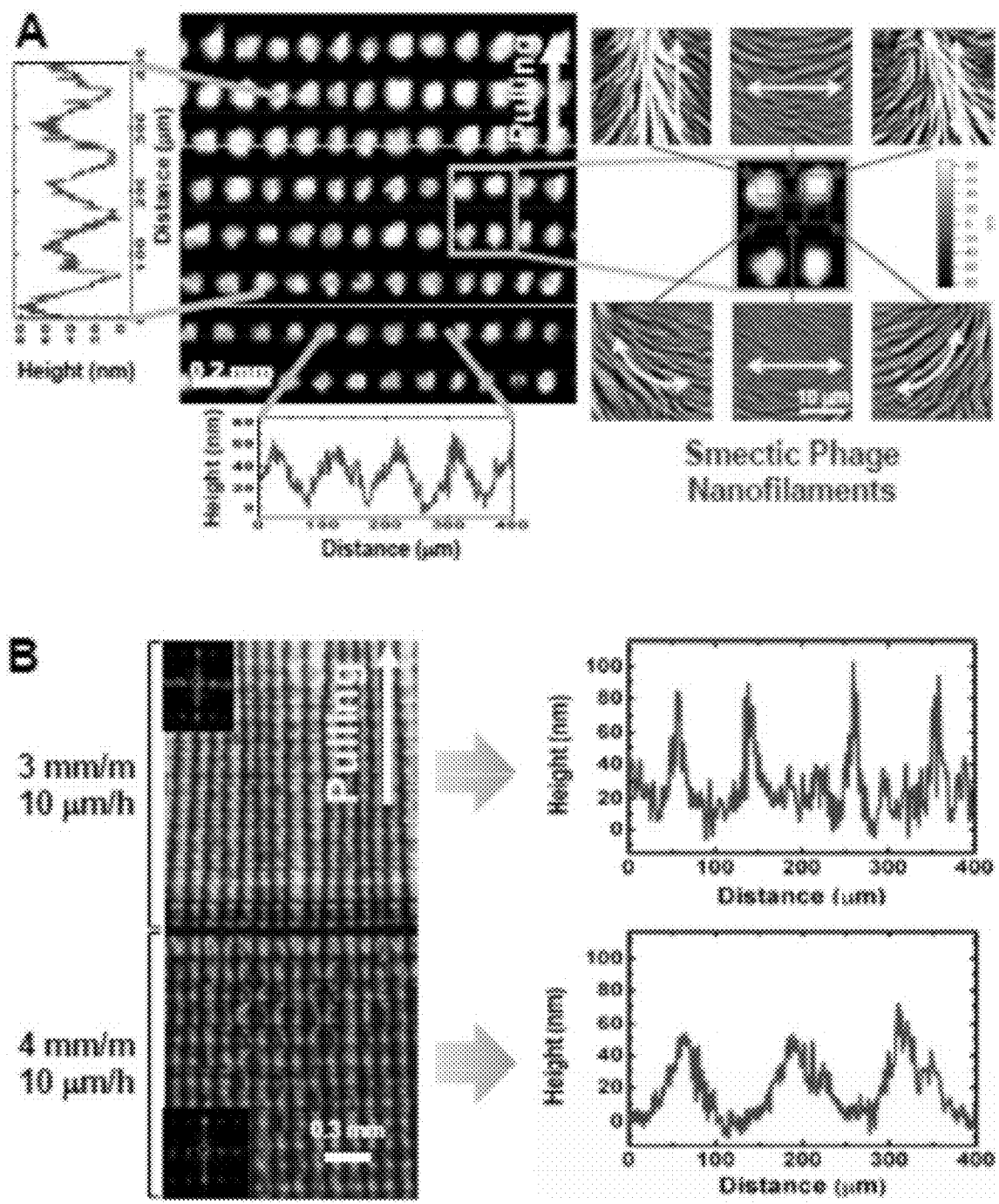
FIG. 12. Single and multi-layered 3D hierarchical structures based on M13 phages fabricated by controlling pulling parameters. (A) Optical images, vertical and horizontal height profiles, and AFM images of phage-based 3D hierarchical structures. (B) Optical images, laser diffraction pattern and vertical height profiles of two-layered hierarchical structures. The resulting films formed periodic structures with even more levels of hierarchical order. The microstructural analysis shown that the film is formed by the cholesteric-like phase of nanofilaments. The individual nanofilaments are composed of smectic phage structures as showed in AFM images which are formed by competing interfacial forces at the meniscus where liquid crystal phase transitions occur. The alpha step measurements along the X-axis and Y-axis confirm the height profiles of the structures. The results clearly show that each periodic dot had more higher than other area.

The resulting structures possess hierarchically organized three-dimensional periodic structures with exquisite optical properties. The films are characterized using a polarized optical microscope (Olympus X71, Olympus Inc, Japan), digital camera (Sony, A70), alpha-step measurement, and an MFP3D AFM (Asylum Research, Santa Barbara, CA) as showed in FIG. 12.

A multi-layered hierarchical structure can be provided by controlling pulling parameters. For example, two-layered hierarchical phage film is created by controlling fast pulling speed in the assembly process. As the pulling speed is increased, the Y-axis interspacing of the film is also increased. Each layer exhibits different colors based on their structure morphology or thickness. By increasing the pulling speed, the matrix thickness is decreased and the generated color is blue shifted from orange to light blue. It can be confirmed by laser diffraction and alpha-step measurements. The laser diffraction pattern clearly show the two-dimensional periodicity. As Y-axis interspacing is increased, the corresponding laser diffraction pattern is narrowed into Y axis. And, as you can see the height profile by alpha-step, the height is decreased with increasing pulling speed, resulting in blue-shift of the generating color.

Figure 13:
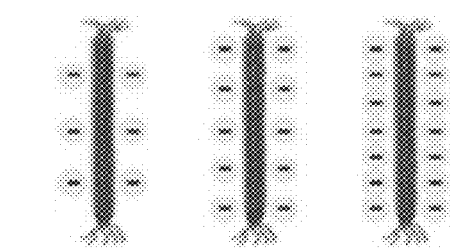
FIG. 13. The 3D hierarchical structures are tunable by varying thermodynamic and kinetic parameters. (A) Relation between X-axis spacing and engineered phages with different surface charges. (B) Relation between X-axis spacing and ionic concentration. (C) Relation between Y-axis spacing and pulling speed. (D) Relation between Y-axis spacing and pulling time. As the surface charges, effective diameter, pulling speed and pulling time are increased, the X- and Y-axis interspacing of the hierarchical structures are increased.
Figure 13:
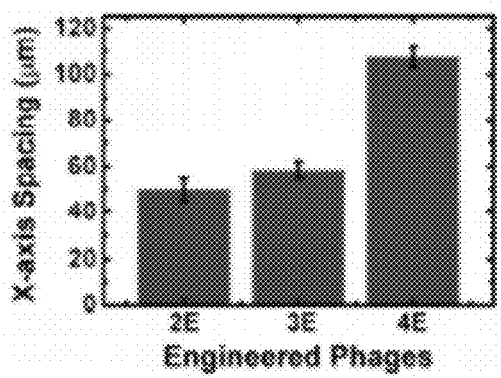
Figure 13:
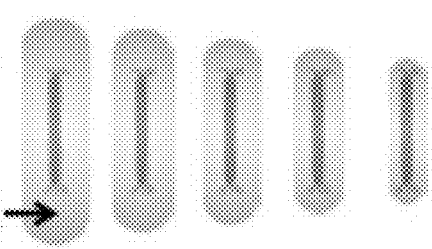
Figure 13:
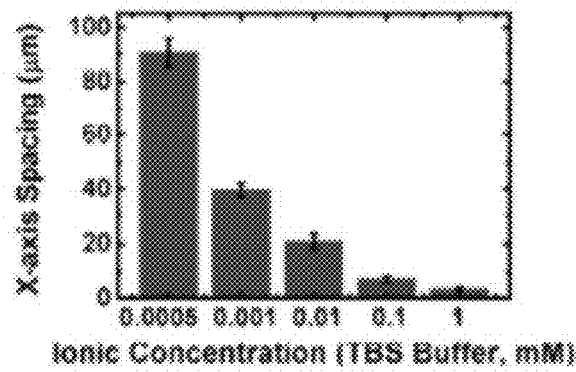
Figure 13:
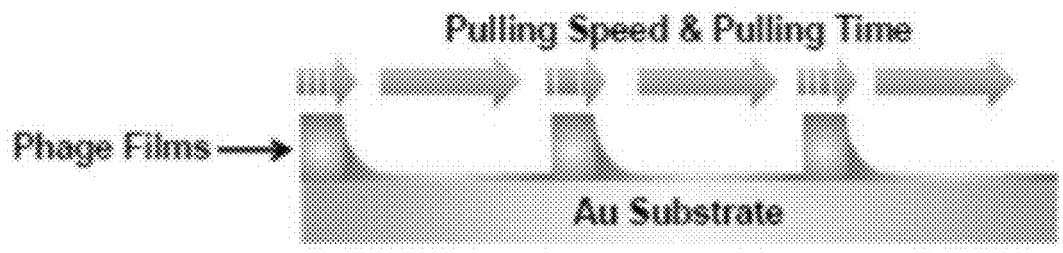
Figure 13:
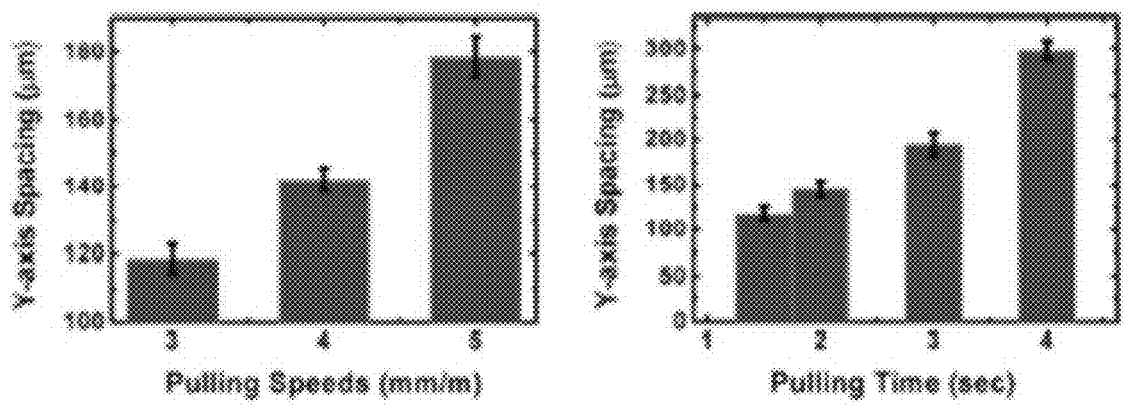

These self-assembled multi-dimensional hierarchical structures are tunable by varying parameters that affect the kinetics and thermodynamics of self-assembly, such as pulling speed, pulling time, surface charge of phages and ionic concentration. Especially, Y-axis interspacing can be controlled by kinetics. As the pulling speed and pulling time are increased, the Y-axis interspacing is also increased. On the other hand, the interspacing of X-axis is tuned by the thermodynamic properties of phage assembly, such as surface charge of phages and ionic concentration. As the surface charges and effective diameter are increased, the X-axis interspacing of the hierarchical structures is also increased. Through the interplay of these factors during the film growth process, one can create tunable hierarchical structures in a controlled manner. FIGS. 13 (A) and (B) show the relationship between the Y-axis interspacing and kinetic parameters of self-assembly. As the pulling speed is increased, the Y-axis interspacing is also increased. In the same manner, the Y-axis interspacing is also increased with increasing pulling time. On the other hand, FIGS. 13 (C) and (D) show the relationship between the x-axis interspacing and thermodynamic parameters of pulling. The interspacing of X-axis originate from the coalescence of phage nanofilaments by 'Rayleigh instability'. Therefore, the surface tension applied on nanofilaments has a significant effect on the variations of X-axis interspacing. At first, the surface charges of phages are tuned by genetic engineering. In this example, the engineered phages with two, three and four glutamic acids on their coat protein are used to increase surface charges of the phages. The surface tension of phage nanofilaments is increased by increasing the surface charges of phages, which increases the x-axis interspacing. The ionic concentration of phage suspensions can also be changed. The effective surface charge density is increased as the ionic concentration is decreased. The increased surface charges interacts with polar solvent (D.I. water), resulting in the increase of surface tension and interspacing.

Figure 14:
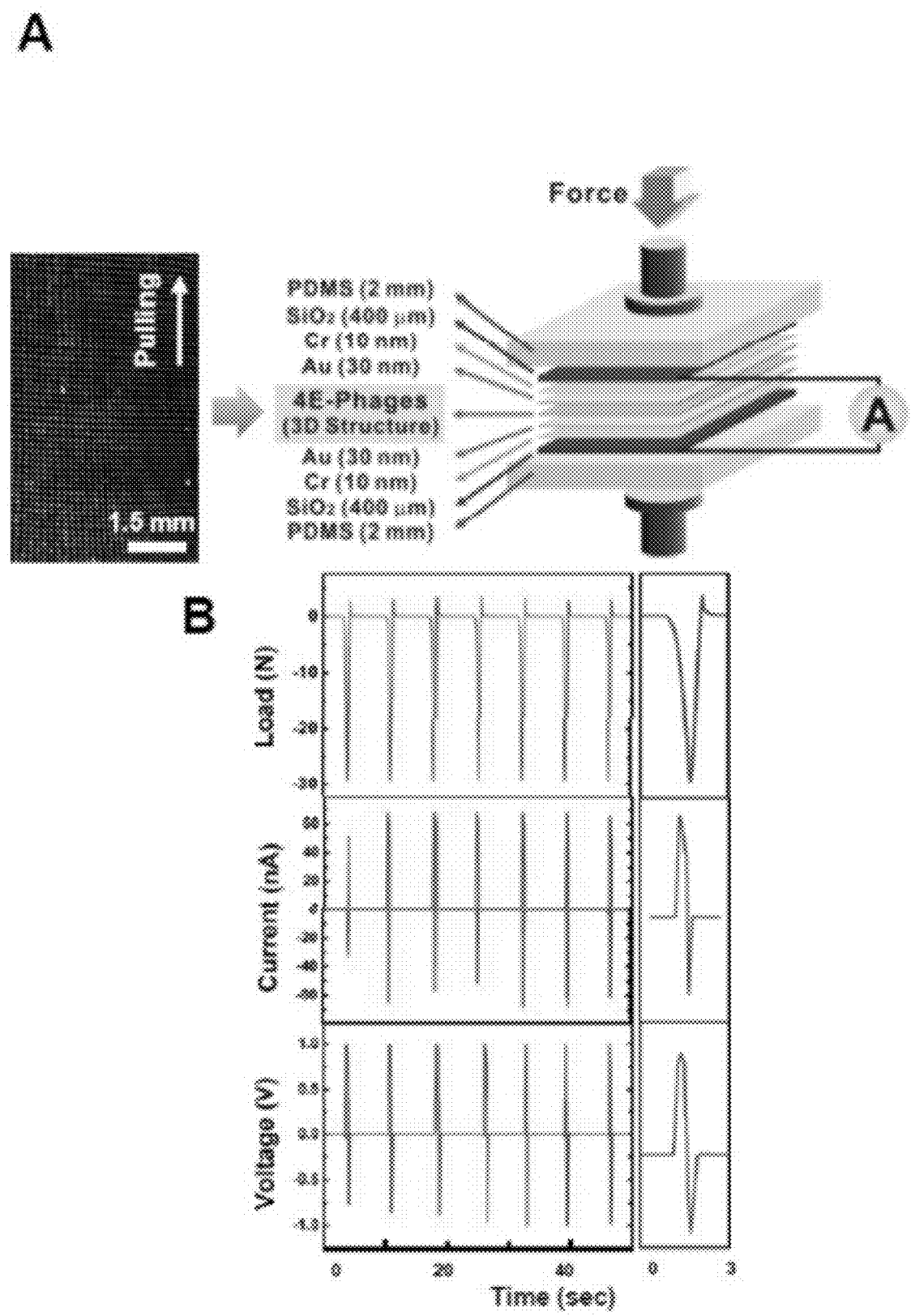
FIG. 14. Piezoelectric energy generators fabricated based on the 3D hierarchical structures. The piezoelectric properties are increased several times than previous phage film-based piezoelectric devices. (A) Piezoelectric device based on the 3D hierarchical phage structure. (B) Mechanical stress applied onto the device, short-circuit current signal, and open-circuit voltage signal from 3D phage structure-based energy generators.

These novel hierarchical structures are useful in many ways. Especially, to demonstrate the practical applications of these structures, piezoelectric energy generators based on the hierarchical 3D phage structures are fabricated. Specifically, M13 phage is covered by ~2,700 copies of a major coat protein (pVIII) and minor coat proteins (pIII and pIX) located at either end. The pVIII proteins have an α-helical structure with a dipole moment from the amino- to carboxyterminal direction and cover the phage body with five-fold rotational symmetry. Because M13's aligned protein coat structure lacks inversion symmetry, the phage is expected to possess intrinsic piezoelectric properties. Periodic mechanical loads are applied to the phage-based piezoelectric generators using a dynamic mechanical test system and the resultant electrical output signal is characterized by measuring the short-circuit current, open-circuit voltage, and charge (FIG. 14 (B)). When applying a compressive load, the signal shows two peaks of reverse polarity, which correspond to the pressing and releasing motion of the mechanical test system. From this example, peak values of ~60 nA for the short-circuit current are typically observed, when a peak load of F=30 N is applied. The open-circuit voltage shows a peak voltage value of about 1 V. The piezoelectric properties are increased several times than previous phage film-based piezoelectric devices. It can enhance the power due to the uniformity of films, phage alignment effect of our structures, and connections between each dots of the 3D structures and Au electrode in parallel configurations.

In summary, a novel biomimetic mesoscale-hierarchical patterning strategy is developed by using meniscus forces driven coalescence of M13 phages. The multi-dimensional hierarchical structures are fabricated from a single type of viral building block in a controlled manner. These phage-based hierarchical microstructures can enhance the power of phage-based piezoelectric energy generations. This bio-inspired self-assembly strategy may provide the way to fabricate large-scale advanced micro electronic or optical devices and biomedical applications in the future.

Methods

Genetic engineering of phage. Engineered phages are constructed using recombinant DNA engineering methods. Different numbers of glutamates are expressed at the N-terminus of the M13 major coat protein, positioned between the first and fifth amino acids of wild-type pVIII, replacing residues 2-4. The constructed phages are amplified using *E. coli* cultures, purified using polyethylene glycol precipitation, and filtered through 0.45 μm pore size membranes. To verify phage stability, DNA sequences are confirmed at each step of the amplification.

Self-templating film fabrication. A phage deposition apparatus is constructed by modifying a syringe pump. A labview program is created to manipulate the motor speed and time controlled through an RS232C cable. Varying phage concentrations, ionic concentrations, pulling speeds and substrate surface chemistries are used for film fabrication. Gold-coated silicon substrates are used unless otherwise described.

Fabrication of phage-based piezoelectric generators. Gold-coated substrates are prepared by depositing 10 nm Cr and 30 nm Au on $SiO_2$ substrates. Then, multi-dimensional hierarchical structures are provided by the self-templated assembly method. After preparation of 3D hierarchical film, another gold-coated substrate is overlaid on the film. The device is then embedded between two ~2.5 mm thick PDMS matrices for structural stability. Signal wires are then soldered onto the gold electrodes.

Piezoelectric generator characterization. The phage-piezoelectric device is mounted onto a dynamic mechanical test system (Electroforce 3200, Bose, MN) and a predefined displacement is applied while monitoring the total force on the device with a load cell. The actual displacement is monitored by a linear variable differential transformer (LVDT) installed in the Electroforce 3200. The force values from the load cell are multiplied by the ratio of the phage film area to the total device area to obtain the effective load applied to the phage film. The open-circuit voltages and short-circuit currents are measured with a semiconductor parameter analyzer (4200-SCS, Keithley, OH, USA).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A piezoelectric device for energy generation or actuation comprising a piezoelectric element comprising a virus comprising a viral capsid comprising a coat protein recombinantly modified to comprise a negatively charged amino acid sequence within the first 50 amino acid residues of the viral capsid's N-terminus; wherein the negatively charged amino acid sequence is three to ten amino acid residues long, does not comprise any positively charged amino acid residue, and comprises at least two negatively charged amino acid residues, wherein each negatively charged amino acid residue is a glutamate or aspartate, and the negatively charged amino acid sequence is displayed on the recombinant virus's surface and does not interfere with the self-assembly of the virus.

2. The device of claim 1, wherein the virus has a helical, icosahedral, or complex symmetry.

3. The device of claim 2, wherein the virus has a filamentous shape.

4. The device of claim 3, wherein the virus is bacteriophage M13.

5. The device of claim 1, wherein the virus capsid comprises an array of repeating coat protein.

6. The device of claim 5, wherein the virus is bacteriophage M13 and the coat protein is pVIII.

7. The device of claim 5, wherein the repeating coat protein has an α-helix structure.

8. The device of claim 5, wherein the repeating coat protein is capable of self-assembly into the array.

9. The device of claim 5, wherein the array is a film of the coat protein comprising a first surface and a second surface.

10. The device of claim 9, wherein the array is a film of the coat protein comprising a first electrode in contact with the first surface and a second electrode in contact with the second surface.

11. The device of claim 10, wherein the first electrode and the second electrode are in electrical communication.

12. A method of making a device of claim 1, comprising:
(a) providing a plurality of suitable virus,
(b) assembling of the plurality of suitable virus into a monolayer of the plurality on a suitable substrate, and
(c) optionally assembling the monolayer into a plurality of two or more monolayers.

13. The method of claim 12, wherein the substrate is a flexible substrate.

14. The method of claim 12, wherein the substrate is a rigid substrate.

15. The method of claim 12, further comprising a preparing step prior to the assembling step.

16. The method of claim 15, wherein the preparing step comprises passivating the substrate by contacting the substrate with a passivating agent.

17. The method of claim 16, wherein the passivating agent is octadecanethiol (ODT) and/or aminothiol.

18. The method of claim 17, wherein the aminothiol is cysteamine.

19. The method of claim 12, wherein the substrate comprises prepatterned electrodes.

20. A method of generating electricity, comprising: (a) providing a piezoelectric device of claim 1, and (b) applying a mechanical pressure to the piezoelectric element of the device such that electricity is produced.

21. The method of claim 20, wherein the mechanical pressure is applied in a vertical direction.

22. The method of claim 20, wherein the mechanical pressure is applied in a shear direction.

23. The piezoelectric device of claim 1, wherein the negatively charged amino acid sequence comprises EE.

24. The piezoelectric device of claim 1, wherein the negatively charged amino acid sequence comprises SEQ ID NO: 10.

25. The piezoelectric device of claim 23, wherein the negatively charged amino acid sequence comprises EEG.

26. The piezoelectric device of claim 25, wherein the negatively charged amino acid sequence comprises SEQ ID NO:11.

27. The piezoelectric device of claim 23, wherein the negatively charged amino acid sequence comprises EEE.

28. The piezoelectric device of claim 27, wherein the negatively charged amino acid sequence comprises SEQ ID NO:12.

29. The piezoelectric device of claim 27, wherein the negatively charged amino acid sequence comprises SEQ ID NO:1.

30. The piezoelectric device of claim 27, wherein the negatively charged amino acid sequence comprises SEQ ID NO:2.

31. The piezoelectric device of claim 30, wherein the negatively charged amino acid sequence comprises SEQ ID NO:13.

* * * * *

SEQUENCE LISTING

<160> NUMBER OF SEQ ID NOS: 13

<210> SEQ ID NO 1
<211> LENGTH: 4
<212> TYPE: PRT

-continued

```
<213> ORGANISM: Artificial sequence
<220> FEATURE:
<223> OTHER INFORMATION: Engineered negatively charged amino acid
      sequence

<400> SEQUENCE: 1

Glu Glu Glu Gly
1

<210> SEQ ID NO 2
<211> LENGTH: 4
<212> TYPE: PRT
<213> ORGANISM: Artificial sequence
<220> FEATURE:
<223> OTHER INFORMATION: Engineered negatively charged amino acid
      sequence

<400> SEQUENCE: 2

Glu Glu Glu Glu
1

<210> SEQ ID NO 3
<211> LENGTH: 5
<212> TYPE: PRT
<213> ORGANISM: Artificial sequence
<220> FEATURE:
<223> OTHER INFORMATION: Engineered phage

<400> SEQUENCE: 3

Ala Glu Gly Asp Asp
1               5

<210> SEQ ID NO 4
<211> LENGTH: 6
<212> TYPE: DNA
<213> ORGANISM: Artificial sequence
<220> FEATURE:
<223> OTHER INFORMATION: Restriction site

<400> SEQUENCE: 4 ctgcag                                                                 6

<210> SEQ ID NO 5
<211> LENGTH: 41
<212> TYPE: DNA
<213> ORGANISM: Artificial sequence
<220> FEATURE:
<223> OTHER INFORMATION: Primer

<400> SEQUENCE: 5
atatatctgc agctgcagag ggcgaccccg caaaagcggc c                          41

<210> SEQ ID NO 6
<211> LENGTH: 44
<212> TYPE: DNA
<213> ORGANISM: Artificial sequence
<220> FEATURE:
<223> OTHER INFORMATION: Primer

<400> SEQUENCE: 6
atatatctgc agctgcagag gagggcgacc ccgcaaaagc ggcc                       44

<210> SEQ ID NO 7
<211> LENGTH: 47
<212> TYPE: DNA
<213> ORGANISM: Artificial sequence
<220> FEATURE:
```

<223> OTHER INFORMATION: Primer

<400> SEQUENCE: 7
atatatctgc agctgcagag gaagagggcg accccgcaaa agcggcc      47

<210> SEQ ID NO 8
<211> LENGTH: 47
<212> TYPE: DNA
<213> ORGANISM: Artificial sequence
<220> FEATURE:
<223> OTHER INFORMATION: Primer

<400> SEQUENCE: 8
atatatctgc agctgcagag gaagaggagg accccgcaaa agcggcc      47

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
cctctgcagc gaaagacagc atcgg      25

<210> SEQ ID NO 10
<211> LENGTH: 5
<212> TYPE: PRT
<213> ORGANISM: Artificial sequence
<220> FEATURE:
<223> OTHER INFORMATION: Engineered phage

<400> SEQUENCE: 10

Ala Glu Gly Asp Pro
1               5

<210> SEQ ID NO 11
<211> LENGTH: 6
<212> TYPE: PRT
<213> ORGANISM: Artificial sequence
<220> FEATURE:
<223> OTHER INFORMATION: Engineered phage

<400> SEQUENCE: 11

Ala Glu Glu Gly Asp Pro
1               5

<210> SEQ ID NO 12
<211> LENGTH: 7
<212> TYPE: PRT
<213> ORGANISM: Artificial sequence
<220> FEATURE:
<223> OTHER INFORMATION: Engineered phage

<400> SEQUENCE: 12

Ala Glu Glu Glu Gly Asp Pro
1               5

<210> SEQ ID NO 13
<211> LENGTH: 7

-continued

```
<212> TYPE: PRT
<213> ORGANISM: Artificial sequence
<220> FEATURE:
<223> OTHER INFORMATION: Engineered phage

<400> SEQUENCE: 13

Ala Glu Glu Glu Glu Asp Pro
1               5
```